(12) United States Patent
Buelna

(10) Patent No.: US 12,161,379 B2
(45) Date of Patent: *Dec. 10, 2024

(54) TREATMENT OF KIDNEY DISEASE USING RENAL NERVE DENERVATION VIA THE RENAL PELVIS

(71) Applicant: Verve Medical, Inc., Paradise Valley, AZ (US)

(72) Inventor: Terrence J. Buelna, Sunset Beach, CA (US)

(73) Assignee: Verve Medical, Inc., Paradise Valley, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/412,229

(22) Filed: Jan. 12, 2024

(65) Prior Publication Data

US 2024/0148423 A1 May 9, 2024

Related U.S. Application Data

(63) Continuation of application No. 18/374,601, filed on Sep. 28, 2023, which is a continuation-in-part of (Continued)

(51) Int. Cl.
*A61B 18/14* (2006.01)
*A61B 18/00* (2006.01)
(Continued)

(52) U.S. Cl.
CPC .............. *A61B 18/00* (2013.01); *A61B 18/08* (2013.01); *A61B 18/1492* (2013.01);
(Continued)

(58) Field of Classification Search
CPC ......... A61B 18/00; A61B 18/14; A61B 18/08; A61B 18/18; A61B 18/04; A61M 25/10; A61N 7/02
See application file for complete search history.

(56) References Cited

U.S. PATENT DOCUMENTS

| 5,370,677 A | 12/1994 | Rudie et al. |
| 6,607,477 B1 | 8/2003 | Longton et al. |

(Continued)

FOREIGN PATENT DOCUMENTS

| CN | 101084038 A | 12/2007 |
| CN | 101426551 | 5/2009 |

(Continued)

OTHER PUBLICATIONS

Kopp, U. C. (2011). Neural control of renal function, Colloquium Series in Integrated Systems Physiology: From Molecule to Function, Morgan & Claypool Life Sciences. (Submitted as Exhibit B to the DiBona Declaration on Feb. 28, 2024).

(Continued)

*Primary Examiner* — Michael F Peffley
*Assistant Examiner* — Amanda L Zink
(74) *Attorney, Agent, or Firm* — Gardella Grace P.A.

(57) ABSTRACT

In an illustrative embodiment, systems and methods for treating kidney disease in a human patient are disclosed. A method includes advancing a collapsible array of RF electrodes through a urinary tract of the patient in collapsed form and into a position in or near a renal pelvis. The effector is deployed to an expanded form to engage at least a portion of an interior wall of the renal pelvis. RF energy delivered through the array of electrodes target afferent nerves proximate the interior wall of the renal pelvis to inhibit or destroy their function. eGFR of the patient can be raised after treatment according to the method.

11 Claims, 18 Drawing Sheets

Related U.S. Application Data application No. 18/175,063, filed on Feb. 27, 2023, which is a continuation of application No. 17/016,232, filed on Sep. 9, 2020, now abandoned, which is a continuation of application No. 16/444,217, filed on Jun. 18, 2019, now Pat. No. 10,786,295, which is a continuation of application No. 13/547,486, filed on Jul. 12, 2012, now Pat. No. 10,357,302.

(60) Provisional application No. 63/410,840, filed on Sep. 28, 2022, provisional application No. 61/506,976, filed on Jul. 12, 2011.

(51) Int. Cl.
   *A61B 18/08* (2006.01)
   *A61B 18/18* (2006.01)
   *A61M 25/10* (2013.01)
   *A61N 7/02* (2006.01)
   *A61B 18/04* (2006.01)

(52) U.S. Cl.
   CPC ......... *A61B 18/1815* (2013.01); *A61M 25/10* (2013.01); *A61N 7/022* (2013.01); *A61B 2018/0016* (2013.01); *A61B 2018/0022* (2013.01); *A61B 2018/00267* (2013.01); *A61B 2018/00291* (2013.01); *A61B 2018/00404* (2013.01); *A61B 2018/00434* (2013.01); *A61B 2018/00511* (2013.01); *A61B 2018/044* (2013.01); *A61B 2018/046* (2013.01); *A61B 2018/143* (2013.01); *A61B 2018/1475* (2013.01)

(56) References Cited

U.S. PATENT DOCUMENTS

| | | |
|---|---|---|
| 7,653,438 B2 | 1/2010 | Deem et al. |
| 7,717,948 B2 | 5/2010 | Demarais et al. |
| 8,137,274 B2 | 3/2012 | Weng et al. |
| 8,167,805 B2 | 5/2012 | Emery et al. |
| 8,277,398 B2 | 10/2012 | Weng et al. |
| 8,295,912 B2 | 10/2012 | Gertner |
| 8,372,009 B2 | 2/2013 | Emery et al. |
| 8,374,674 B2 | 2/2013 | Gertner |
| 8,388,535 B2 | 3/2013 | Weng et al. |
| 8,469,904 B2 | 6/2013 | Gertner |
| 8,512,262 B2 | 8/2013 | Gertner |
| 8,517,962 B2 | 8/2013 | Gertner et al. |
| 8,548,600 B2 | 10/2013 | Deem et al. |
| 8,556,834 B2 | 10/2013 | Gertner |
| 8,622,937 B2 | 1/2014 | Weng et al. |
| 8,715,209 B2 | 5/2014 | Gertner |
| 9,668,811 B2 | 6/2017 | Sogard et al. |
| 10,357,302 B2 | 7/2019 | Buelna |
| 10,786,295 B2 | 9/2020 | Buelna |
| 2002/0048310 A1 | 4/2002 | Heuser |
| 2003/0153905 A1 | 8/2003 | Edwards et al. |
| 2003/0216792 A1 | 11/2003 | Levin et al. |
| 2006/0235474 A1 | 10/2006 | Demarais |
| 2006/0276852 A1 | 12/2006 | Demarais et al. |
| 2007/0129720 A1 | 6/2007 | Demarais et al. |
| 2008/0086073 A1 | 4/2008 | McDaniel |
| 2008/0228209 A1 | 9/2008 | DeMello et al. |
| 2009/0192485 A1 | 7/2009 | Heuser |
| 2010/0168731 A1 | 7/2010 | Wu et al. |
| 2011/0015648 A1 | 1/2011 | Alvarez et al. |
| 2011/0060324 A1 | 3/2011 | Wu et al. |
| 2011/0104061 A1 | 5/2011 | Seward |
| 2011/0301662 A1* | 12/2011 | Bar-Yoseph ....... A61N 1/36007 607/40 |
| 2012/0029513 A1 | 2/2012 | Smith et al. |
| 2012/0065554 A1 | 3/2012 | Pikus |
| 2012/0078160 A1 | 3/2012 | McMillan |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0123303 A1 | 5/2012 | Sogard et al. |
| 2012/0130368 A1 | 5/2012 | Jenson |
| 2013/0053732 A1 | 2/2013 | Heuser |
| 2013/0165764 A1 | 6/2013 | Scheuermann et al. |
| 2013/0165926 A1 | 6/2013 | Mathur et al. |
| 2013/0178824 A1 | 7/2013 | Buelna |
| 2014/0074083 A1 | 3/2014 | Horn et al. |
| 2014/0107639 A1 | 4/2014 | Zhang et al. |
| 2015/0065783 A1* | 3/2015 | Buelna ................. A61B 18/04 606/41 |
| 2015/0223866 A1 | 8/2015 | Buelna et al. |
| 2015/0342531 A1 | 12/2015 | Hoitink et al. |
| 2018/0325587 A1 | 11/2018 | Buelna |
| 2019/0329042 A1* | 10/2019 | DiLorenzo ......... A61N 1/36103 |
| 2020/0405368 A1 | 12/2020 | Buelna |
| 2021/0077419 A1 | 3/2021 | Buelna et al. |
| 2021/0121218 A1 | 4/2021 | Buelna |
| 2023/0218331 A1 | 7/2023 | Buelna |
| 2024/0024013 A1 | 1/2024 | Buelna |
| 2024/0099988 A1 | 3/2024 | Buelna |
| 2024/0148423 A1 | 5/2024 | Buelna |
| 2024/0189253 A1 | 6/2024 | Buelna |

FOREIGN PATENT DOCUMENTS

| | | |
|---|---|---|
| CN | 101583323 | 11/2009 |
| DE | 19701840 A1 | 11/1997 |
| EP | 2747830 A1 | 7/2014 |
| JP | 2013544133 A | 12/2013 |
| WO | 9103996 | 4/1991 |
| WO | 97/44088 A1 | 11/1997 |
| WO | 2005000130 | 1/2005 |
| WO | 2007078997 A2 | 7/2007 |
| WO | 2009097294 A1 | 8/2009 |
| WO | 2010067360 A2 | 6/2010 |
| WO | 2010067360 A3 | 9/2010 |
| WO | 2011046880 | 4/2011 |
| WO | 2011053757 A1 | 5/2011 |
| WO | 2011082278 A1 | 7/2011 |
| WO | 2011112400 A1 | 9/2011 |
| WO | 2012/061161 A1 | 5/2012 |
| WO | 2012170482 A1 | 12/2012 |
| WO | 2013/010009 A1 | 1/2013 |
| WO | 2013010009 | 1/2013 |
| WO | 2013028812 A1 | 2/2013 |
| WO | 2013/134469 A1 | 9/2013 |
| WO | 2013134469 | 9/2013 |
| WO | 2015/120340 A1 | 8/2015 |

OTHER PUBLICATIONS

DiBona, G. F., & Esler, M. (2010). Translational medicine: the antihypertensive effect of renal denervation. American Journal of Physiology—Regulatory, Integrative and Comparative Physiology, 298(2), R245-R253. (Submitted as Exhibit C to the DiBona Declaration on Feb. 28, 2024).

Esler, M. (2011). The sympathetic nervous system through the ages: from Thomas Willis to resistant hypertension. Experimental physiology, 96(7), 611-622. (Submitted as Exhibit D to the DiBona Declaration on Feb. 28, 2024).

Vase, H., Mathiassen, O. N., Kaltoft, A., Pedersen, E. B., Christensen, K. L., Buus, N. H., . . . & Thuesen, L. (2012). Catheter-based renal denervation for treatment of resistant hypertension. Dan Med J, 59(6), A4439. (Submitted as Exhibit E to the DiBona Declaration on Feb. 28, 2024).

Zhang, Y., Hata, C., & De La Rama, A., Certified U.S. Appl. No. 61/493,849, filed Jun. 6, 2011, entitled "Renal Denervation System and Method," 17 pages. (Submitted as Exhibit F to the DiBona Declaration on Feb. 28, 2024).

Tunev, S. S., & Trudel, J., File History of U.S. Appl. No. 61/608,022, filed Mar. 7, 2012, entitled "Selective Modulation of Renal Nerves," 58 pages. (Submitted as Exhibit H to the DiBona Declaration on Feb. 28, 2024).

(56) References Cited

OTHER PUBLICATIONS

Mitterberger, M., Pinggera, G. M., Feuchtner, G., Neururer, R., Bartsch, G., Gradl, J., . . . & Frauscher, F. (2007). Sonographic measurement of renal pelvis wall thickness as diagnostic criterion for acute pyelonephritis in adults. Ultraschall in der Medizin—European Journal of Ultrasound, 28(06), 593-597. (Submitted as Exhibit I to the DiBona Declaration on Feb. 28, 2024).
Weizer, A. Z., Raj, G. V., O'Connell, M., Robertson, C. N., Nelson, R. C., & Polascik, T. J. (2005). Complications after percutaneous radiofrequency ablation of renal tumors. Urology, 66(6), 1176-1180. (Submitted as Exhibit K to the DiBona Declaration on Feb. 28, 2024).
Gervais, D. A., Arellano, R. S., McGovern, F. J., McDougal, W. S., & Mueller, P. R. (2005). Radiofrequency ablation of renal cell carcinoma: part 2, Lessons learned with ablation of 100 tumors. American Journal of Roentgenology, 185(1), 72-80. (Submitted as Exhibit M to the DiBona Declaration on Feb. 28, 2024).
Caliskan, S., & Cevik, R. (2016). Retroperitoneal urinoma after percutaneous nephrolithotomy. Medicine Science, 5(2), 720-724. (Submitted as Exhibit N to the DiBona Declaration on Feb. 28, 2024).
Sakakura, K., Ladich, E., Cheng, Q., Otsuka, F., Yahagi, K., Fowler, D. R., . . . & Joner, M. (2014). Anatomic assessment of sympathetic peri-arterial renal nerves in man. Journal of the American College of Cardiology, 64(7), 635-643. (Submitted as Exhibit O to the DiBona Declaration on Feb. 28, 2024).
Vink, E. E., Goldschmeding, R., Vink, A., Weggemans, C., Bleijs, R. L., & Blankestijn, P. J. (2014). Limited destruction of renal nerves after catheter-based renal denervation: results of a human case study. Nephrology Dialysis Transplantation, 29(8), 1608-1610. (Submitted as Exhibit P to the DiBona Declaration on Feb. 28, 2024).
Bhatt, D. L., Kandzari, D. E., O'Neill, W. W., D'Agostino, R., Flack, J. M., Katzen, B. T., . . . & Bakris, G. L. (2014). A controlled trial of renal denervation for resistant hypertension. New England Journal of Medicine, 370(15), 1393-1401. (Submitted as Exhibit Q to the DiBona Declaration on Feb. 28, 2024).
Schaeffer, A. J., Kurtz, M. P., Logvinenko, T., McCartin, M. T., Prabhu, S. P., Nelson, C. P., & Chow, J. S. (2016). MRI-based reference range for the renal pelvis anterior-posterior diameter in children ages 0-19 years. The British journal of radiology, 89(1067), Feb. 11, 2016. (Submitted as Exhibit R to the DiBona Declaration on Feb. 28, 2024).
Weber, M. A., Hering, D., Nikoleishvili, D., Imedadze, A., Dughashvili, G., Klimiashvili, Z., . . . & Provanzano, R. (2023). Durability of the Blood Pressure Effects of Renal Pelvis Denervation in Patients with Hypertension During a 12-Month Observation. American Journal of Nephrology. (Submitted as Exhibit S to the DiBona Declaration on Feb. 28, 2024).
Buelna, T. J., & Gold, A., U.S. Appl. No. 62/074,894, filed Nov. 4, 2014, entitled "Methods and Systems for Surface Ablation of the Renal Pelvis," 36 pages.
Non-Final Office Action issued in related U.S. Appl. No. 17/097,387 on Oct. 11, 2022, 13 pages.
Final Office Action issued in related U.S. Appl. No. 17/097,387 on Mar. 27, 2023, 20 pages.
Non-Final Office Action issued in related U.S. Appl. No. 17/097,387 on Oct. 20, 2023, 14 pages.
Non-Final Office Action issued in related U.S. Appl. No. 13/547,486 on Dec. 26, 2014, 11 pages.
Final Office Action issued in related U.S. Appl. No. 13/547,486 on May 6, 2015, 12 pages.
Non-Final Office Action issued in related U.S. Appl. No. 13/547,486 on Feb. 1, 2016, 10 pages.
Final Office Action issued in related U.S. Appl. No. 13/547,486 on Oct. 3, 2016, 10 pages.
Non-Final Office Action issued in related U.S. Appl. No. 13/547,486 on Jun. 29, 2017, 9 pages.
Final Office Action issued in related U.S. Appl. No. 13/547,486 on Apr. 23, 2018, 9 pages.
Notice of Allowance issued in related U.S. Appl. No. 13/547,486 on Jun. 11, 2019, 8 pages.
International Search Report and Written Opinion issued in related International application No. PCT/US2012/046511 on Oct. 2, 2012, 16 pages. (Submitted in related U.S. Appl. No. 13/547,486.).
Non-Final Office Action issued in related U.S. Appl. No. 13/217,233 on Feb. 27, 2013, 10 pages. (Submitted in related U.S. Appl. No. 13/547,486.).
Final Office Action issued in related U.S. Appl. No. 13/217,233 on Jun. 14, 2013, 10 pages. (Submitted in related U.S. Appl. No. 13/547,486.).
Non-Final Office Action issued in related U.S. Appl. No. 13/217,233 on Sep. 25, 2014, 11 pages. (Submitted in related U.S. Appl. No. 13/547,486.).
European Search Report and Opinion issued in related EP application No. 12811672.0 on Dec. 2, 2014, 6 pages. (Submitted in related U.S. Appl. No. 13/547,486.).
International Search Report and Written Opinion issued in related International application No. PCT/US2012/051950 on Jan. 17, 2013, 7 pages. (Submitted in related U.S. Appl. No. 13/547,486.).
Davidson et al., Interventional Approaches for Resistant Hypertension, Current Opinion in Nephrology and Hypertension, 2012, 21(5): 475-480. (Submitted in related U.S. Appl. No. 13/547,486.).
Final Office Action issued in related U.S. Appl. No. 13/217,233 on Apr. 22, 2015, 14 pages. (Submitted in related U.S. Appl. No. 13/547,486.).
Extended European Search Report issued in related EP application No. 12825105.5 on Mar. 9, 2015, 7 pages. (Submitted in related U.S. Appl. No. 13/547,486.).
Non-Final Office Action issued in related U.S. Appl. No. 15/979,222 on Sep. 9, 2020, 6 pages. (Submitted in related U.S. Appl. No. 17/016,232.).
Notice of Allowance issued in related U.S. Appl. No. 16/444,217 on Jun. 12, 2020, 9 pages.
Non-Final Office Action issued in related U.S. Appl. No. 17/016,232 on Mar. 28, 2022, 13 pages.
Final Office Action issued in related U.S. Appl. No. 17/016,232 on Nov. 30, 2022, 14 pages.
Non-Final Office Action issued in related U.S. Appl. No. 14/616,576 on Jun. 13, 2017, 10 pages.
Final Office Action issued in related U.S. Appl. No. 14/616,576 on Jan. 26, 2018, 12 pages.
Non-Final Office Action issued in related U.S. Appl. No. 14/616,576 on Feb. 26, 2019, 10 pages.
Final Office Action issued in related U.S. Appl. No. 14/616,576 on Nov. 13, 2019, 12 pages.
Non-Final Office Action issued in related U.S. Appl. No. 14/616,576 on May 19, 2020, 14 pages.
Extended European Search Report issued in related EP application No. 15746617.8 on Sep. 28, 2017, 5 pages.
Hsu, Mark, et al., Intraoperative Optical Imaging and Tissue Interrogation During Urologic Surgery, Curr Opin Urol., Jan. 2014, 24(1), 66-74, doi: 10.1097/MOU.0000000000000010.
Whitney, Michael A., et al., Fluorescent peptides highlight peripheral nerves during surgery in mice, Nat Biotechnol., Apr. 2011, 29(4), 352-6, doi: 10.1038/nbt.1764. Epub Feb. 6, 2011.
Non-Final Office Action issued in related U.S. Appl. No. 14/809,058 on Jun. 15, 2018, 14 pages.
Final Office Action issued in related U.S. Appl. No. 14/809,058 on Dec. 27, 2018, 9 pages.
Non-Final Office Action issued in related U.S. Appl. No. 14/809,058 on Oct. 25, 2019, 12 pages.
Notice of Allowance issued in related U.S. Appl. No. 14/809,058 on Jun. 21, 2022, 7 pages.
International Search Report and Written Opinion issued in related international application No. PCT/US2015/014926 on Jul. 10, 2015, 12 pages.
Non-Final Office Action issued in related U.S. Appl. No. 17/143,725 on Dec. 29, 2023, 7 pages.
Non-Final Office Action issued in related U.S. Appl. No. 18/412,229 on Apr. 9, 2024, 7 pages.
Non-Final Office Action issued in related U.S. Appl. No. 18/412,240 on Apr. 25, 2024, 17 pages.

(56) References Cited

OTHER PUBLICATIONS

First Office Action and Search Report issued in related CN application No. 2012800442716 on Oct. 16, 2015, 7 pages.
First Office Action issued in related CN application No. 201580018000.7 on Sep. 11, 2018, 11 pages.
Second Office Action issued in related CN application No. 201580018000.7 on Jun. 10, 2019, 9 pages.
Third Office Action issued in related CN application No. 201580018000.7 on Dec. 24, 2019, 10 pages.
Search Report issued in related CN application No. 201580018000.7 on Sep. 11, 2018, 1 page.
Supplemental Search Report issued in related CN application No. 201580018000.7 on Sep. 11, 2018, 11 pages.
First Office Action issued in related CN application No. 2012800522481 on Jun. 2, 2015, 11 pages.
Second Office Action issued in related CN application No. 2012800522481 on Jan. 13, 2016, 8 pages.
Communication pursuant to Article 94(3) EPC issued in related EP application No. 128116723.0 on Dec. 13, 2016, 5 pages.
Opinion and Supplemental Search Report issued in related EP application No. 15746617.8 on Sep. 21, 2017, 4 pages.
Decision of Refusal issued in related JP application No. 2014-520333 on Dec. 13, 2016, 2 pages.
Notice of Reasons for Refusal issued in related JP application No. 2014-520333 on Apr. 14, 2016, 10 pages.
Search Report issued in related JP application No. 2014-520333 on Mar. 17, 2016, 14 pages.
Decision of Refusal issued in related JP application No. 2016-568471 on Feb. 28, 2020, 2 pages.
Notice of Reasons for Refusal issued in related JP application No. 2016-568471 on Oct. 9, 2018, 6 pages.
Notice of Reasons for Refusal issued in related JP application No. 2016-568471 on Jul. 2, 2019, 6 pages.
Search Report issued in related JP application No. 2016-568471 on Sep. 19, 2018, 38 pages.
Written Opinion issued in related JP application No. 2016-568471 on Apr. 11, 2019, 7 pages.
International Preliminary Report on Patentability issued in related international application No. PCT/US2012/046511 on Jan. 14, 2014, 6 pages.
International Preliminary Report on Patentability issued in related international application No. PCT/US2012/051950 on Feb. 25, 2014, 5 pages.
International Preliminary Report on Patentability issued in related international application No. PCT/US2015/014926 on Aug. 9, 2016, 9 pages.

* cited by examiner

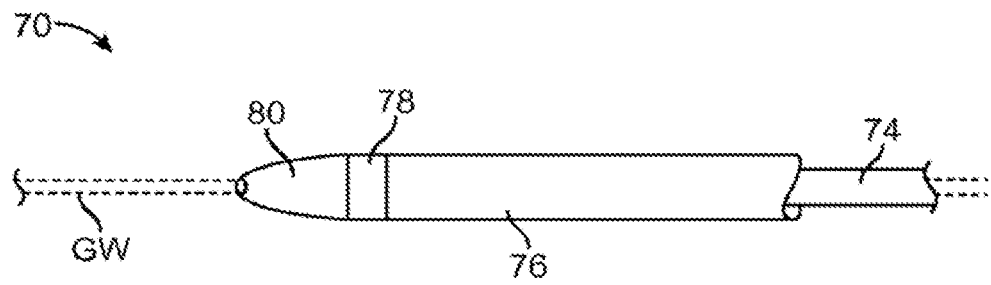
FIG. 7A
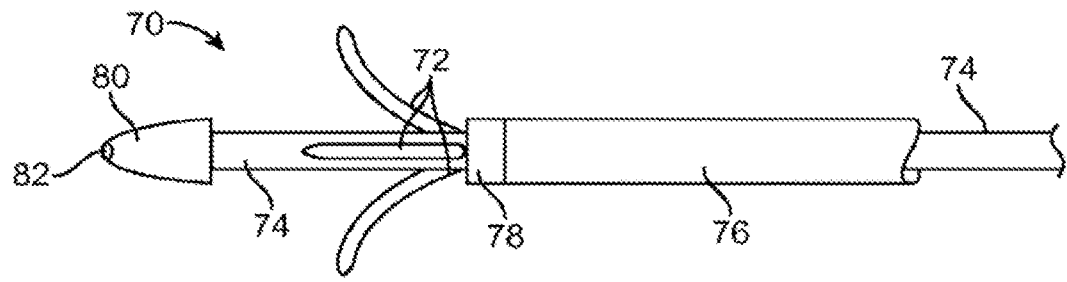
FIG. 7B
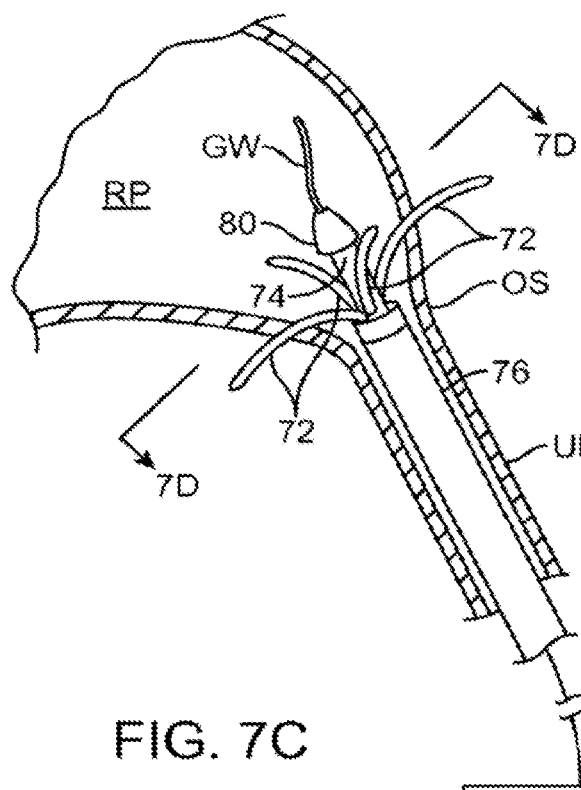
FIG. 7C
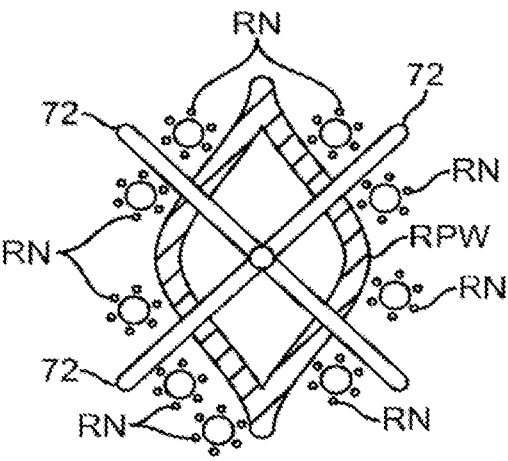
FIG. 7D

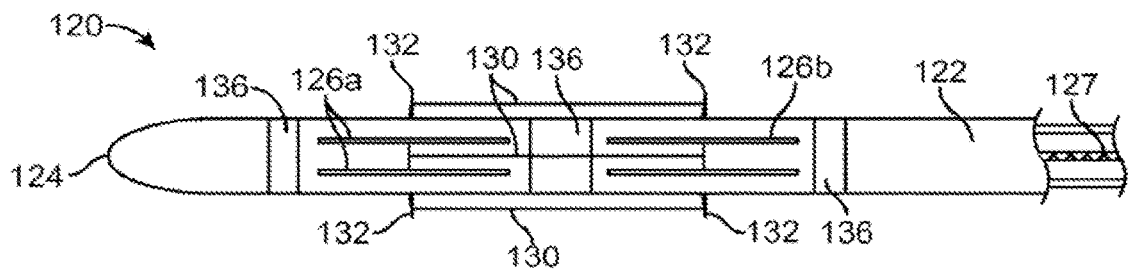
FIG. 10A
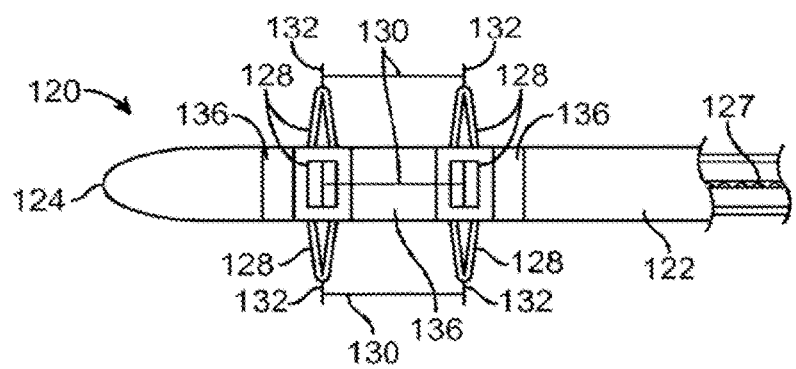
FIG. 10B
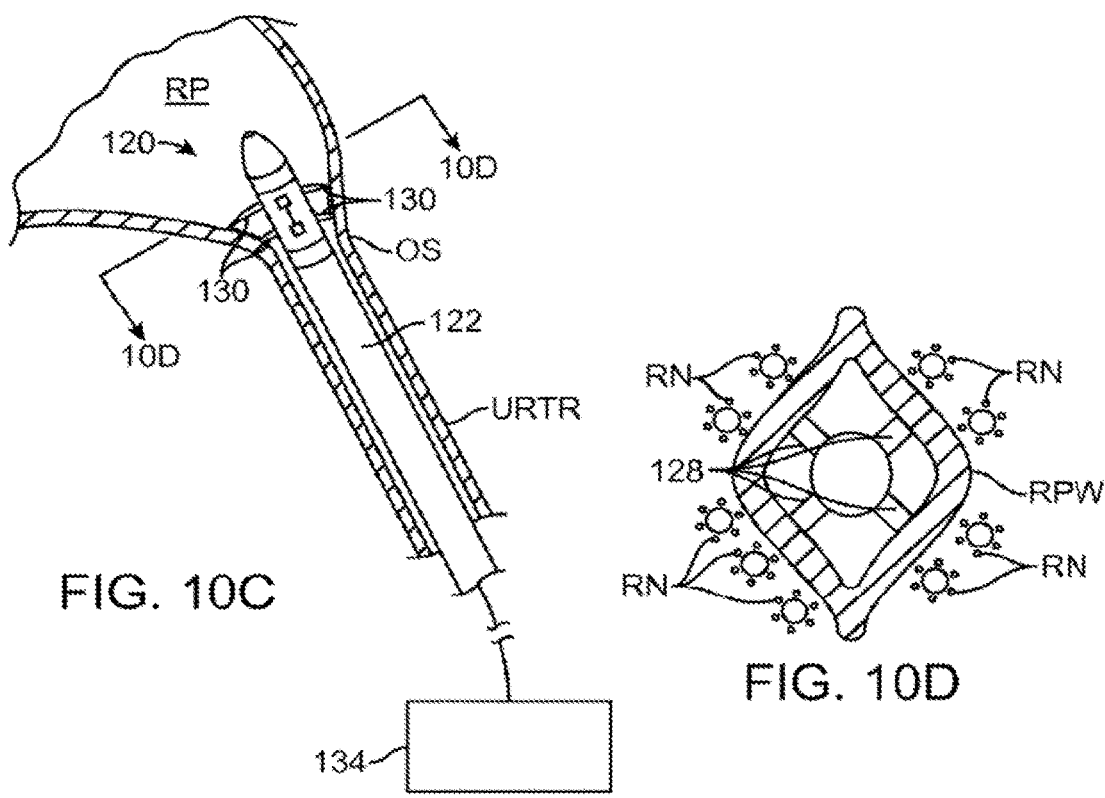
FIG. 10C
FIG. 10D

TREATMENT OF KIDNEY DISEASE USING RENAL NERVE DENERVATION VIA THE RENAL PELVIS

CROSS-REFERENCE TO RELATED APPLICATIONS

This application is a continuation of U.S. patent application Ser. No. 18/374,601, filed Sep. 28, 2023, which is a continuation-in-part of U.S. patent application Ser. No. 18/175,063, filed Feb. 27, 2023, which is a continuation application of U.S. patent application Ser. No. 17/016,232, filed Sep. 9, 2020, which is a continuation application of U.S. patent application Ser. No. 16/444,217, filed Jun. 18, 2019, and now issued as U.S. Pat. No. 10,786,295, which is a continuation application of U.S. patent application Ser. No. 13/547,486, filed Jul. 12, 2012, and now issued as U.S. Pat. No. 10,357,302, which claims the benefit of U.S. Prov. Pat. App. No. 61/506,976, filed Jul. 12, 2011. The entire contents of each of these applications is incorporated herein by reference. This application also claims the benefit of U.S. Patent Application No. 63/410,840, file Sep. 28, 2022.

BACKGROUND

Chronic kidney disease typically results in a gradual loss of kidney function. Healthy kidneys filter waste and excess fluids from your blood, which are then removed in your urine. Advanced chronic kidney disease can cause dangerous levels of fluid, electrolytes and wastes to build up in your body. Chronic kidney disease can have a number of negative patient outcomes including stroke, congestive heart failure (CHF), end stage kidney disease (end stage renal failure), Treatment for chronic kidney disease focuses on slowing the progression of kidney damage, usually by controlling the cause. But even controlling the cause might not keep kidney damage from progressing. Chronic kidney disease can progress to end-stage kidney failure, which is fatal without artificial filtering (dialysis) or a kidney transplant.

Hypertension, or high blood pressure, is a significant and growing health risk throughout the world. Hypertension can be caused by hyperactive renal sympathetic nerves which extend adjacent to the outside of the arteries and veins leading to a patient's kidney as well as within the wall of the renal pelvis. Renal nerve activity can be a significant cause of systemic hypertension, and it has long been known that disrupting renal nerve function can reduce blood pressure. More recently, hypertension therapies based on disrupting the renal nerves surrounding the renal arteries leading to the kidney (renal denervation) have been proposed and are described in the medical and patent literature.

Heretofore, most of the proposed renal denervation therapies have utilized an intravascular approach where a catheter is introduced into the arterial system and advanced to the main renal artery leading to the left or right kidney. Once located at a desired target site within the main renal artery, the catheter is used to deliver radiofrequency energy, heat, drugs, or the like to disrupt the function of the renal nerves which surround the artery. While effective, these techniques present a risk of injury to the renal artery and suffer from all the known disadvantages associated with intravascular access and therapies.

SUMMARY OF ILLUSTRATIVE EMBODIMENTS

The methods and procedures described herein demonstrate that renal pelvic denervation significantly reduces blood pressure in patients with uncontrolled hypertension who were previously taking antihypertensive drugs. In one trial, by two months after the procedure there was a reduction in the 24-hour ambulatory systolic blood pressure of 20.3 mmHg with similar reductions in the daytime and nighttime measurements, indicating a continuous 24-hour blood pressure-lowering effect. Of note, 17 of the 18 patients in the study had reductions in their daytime systolic blood pressure, none had an increase in daytime systolic blood pressure and all 18 had reductions in their 24-hour systolic blood pressure.

During the study, estimated glomerular filtration rate (eGFR) was used to determine a patient's stage of kidney disease and qualify them for treatment. eGFR can be calculated from blood creatinine levels along with age, body size, and gender of the patient. GFR can be calculated in other ways as well.

Surprisingly, the study data further demonstrated a small but significant increase in eGFR and a significant decrease in mean serum creatinine, both of which correlate with a decreased risk of kidney disease and associated morbidities, including a reduced risk of stroke, congestive heart failure, and end-stage renal disease, as well as hormone function, including reductions in renin, aldosterone, and angiotensin. Equivalent observed increases in eGFR and decreases in mean serum creatinine have not generally been observed with intravascular renal nerve ablation, thus affording added therapeutic benefit for renal pelvis ablation.

An exemplary method for treating kidney disease in accordance with an embodiment comprises selecting a patient suffering or at risk of suffering from kidney disease, as indicated by a pre-treatment estimated glomerular filtration rate (eGFR) in a first range. In one embodiment, the pre-treatment eGFR range in which patients are qualified to receive the treatment is a range between 45 and 90 mL/min/1.73 m$^2$. For patients selected to receive treatment, an effector is introduced into an interior of the patient's renal pelvis comprising the patient's kidney or an upper region of a ureter adjacent to the patient's kidney. The effector is used to deliver energy to an interior wall of the renal pelvis, producing an increase in the patient's eGFR in a range from 1 to 100 mL/min/1.73 m$^2$.

In specific instances, the patient experiences an increase in eGFR in a range from 10 to 75 mL/min/1.73 m$^2$. In further specific instances, the patient experiences an increase in eGFR in a range from 10 to 50 mL/min/1.73 m$^2$, often in a range from 10 to 25 mL/min/1.73 m$^2$.

Typically, the patient had a serum creatinine level in a range from 0.95 mg/dL to 1 mg/dL prior to treatment. In specific instances, the patient experiences a decrease in serum creatinine in a range from 0.01 mg/dL to 1 mg/dL. In further specific instances, the patient experiences a decrease in serum creatinine in a range from 0.05 mg/dL to 1 mg/dL, often in a range from 0.1 mg/dL to 1 mg/dL.

In some instances, the patient may also suffer or be at risk of suffering from hypertension, but in many instances, the patient does not have diagnosed hypertension.

Embodiments described herein relate generally to medical devices, systems, apparatus, and methods for modifying nerve function and treating disease. More particularly, embodiments relate to methods and apparatus for exchanging energy or delivering active agents through the renal pelvis to modify sympathetic nerve activity in the adventitia of arteries and/or veins that surround the external surface of the renal pelvis in the kidney and in the afferent and efferent nerves within the muscle layers, urothelium and submucosa of the renal pelvis.

Embodiments described herein provide apparatus, systems, and methods for disrupting, inhibiting, denervating and/or modulating the activity of renal nerves present in a patient's kidney by exchanging energy or delivering active agents or substances to the renal nerves which lie within the wall of the renal pelvis or adjacent to the renal pelvis within the kidney. Most commonly, such renal denervation and/or modulation will be for the purpose of reducing blood pressure in patients suffering from and/or diagnosed with hypertension, but the methods and apparatus can be used for treating patients diagnosed with other conditions as described below. The energy exchange or agent delivery is effected through a wall of the renal pelvis using an effector which has been positioned within the interior of the renal pelvis. The renal blood vessels, including the renal arteries and to a lesser extent the renal veins, enter the kidney in a branching network from the main renal artery and main renal vein leading to the kidney. The renal nerves are present in the adventitial tissue surrounding these branching blood vessels as well as in the tissue bed adjacent to the external wall of the renal pelvis. The renal nerves are also in the wall of the renal pelvis in the form of a dense nerve matrix consisting of both afferent and efferent nerves between the muscle layers as well as within the endothelium and submucosa.

Described embodiments introduce or advance the effector into the interior of the renal pelvis by a minimally invasive approach or access. Usually, the access will be through the urinary tract and thus not require percutaneous penetration (and thus may be performed as a "natural orifice surgery"). Alternatively, the access could be achieved through known laparoscopic or other percutaneous techniques relying on access penetrations through the abdominal wall and advancement of tools through the body of the kidney in order to access the hilum and in turn the renal pelvis. Such laparoscopic techniques are on the one hand disadvantageous because they require such tissue penetrations but on the other hand are advantageous in that they allow introduction and utilization of large tools under direct visualization which would not be possible using a minimally invasive approach via the urinary tract.

Once in the interior of the renal pelvis, the effector will be used to exchange energy and/or deliver active agents or substances to the wall of the renal pelvis and additionally to the tissue bed surrounding the exterior wall of the renal pelvis to effect nerve denervation or modulation. Often, the effector will be an expandable structure, such as an inflatable balloon or mechanically expandable cage, which can be deployed within the renal pelvis to engage at least a portion of interior wall of the renal pelvis, often engaging the entire interior wall of the renal pelvis. Elements for exchanging energy and/or delivering active substances can be present on the outer wall of such expandable structures or may be present within the interior of such expandable structures in order to generate, exchange, and deliver energy and substances as described in more detail below.

Other embodiments of the effector include tissue-penetrating needles and electrodes for delivering or exchanging energy within the wall of the renal pelvis, radiation-emitting sources, such as radioisotopes, electronic radiation emitters, such as X-ray sources, and the like.

In preferred embodiments, the exchange of energy and/or delivery of active substances will be limited to protect structures within the kidney not surrounding the renal pelvis, such as the papillae, the parenchyma, the pyramids, and the like. The energy exchange and/or active substance delivery may optionally extend into an upper portion or region of the ureter, and in some cases it may be possible to position a microwave antennae, ultrasound transducer, or other energy transmitter entirely within the ureter to direct energy toward the nerves within and adjacent to the renal pelvis, e.g., within the ureteral pelvic junction (UPJ). Limiting the therapies to avoid such sensitive kidney structures surrounding the renal pelvis limits or eliminates damaging such structures and adversely impacting renal function.

Thus, in a first aspect, the embodiments provide methods for inhibiting or modulating the function of renal nerves in a patient's kidney. The purpose of the inhibition or modulation could be for treating systemic hypertension, chronic kidney disease, chronic heart disease, sleep apnea, chronic pain, polycystic kidney disease, insulin resistance, obesity, benign prostate hyperplasia, (BPH), or for other purposes. The method is carried out by introducing an effector into an interior of the kidney and exchanging energy and/or delivering active substances from the interior of the kidney through a wall of the renal pelvis to the renal nerves within the pelvic wall as well as surrounding the renal blood vessels within the kidney or UPJ. In many embodiments, the methods will rely on delivering energy to raise the temperature of the renal pelvis and the tissue bed surrounding the blood vessels to a temperature within a target range sufficient to inhibit or destroy nerve function (denervation) typically being in the range from 45° C. to 80° C., usually in the range from 45° C. to 60° C., typically for a time in the range from 3 sec. to 4 minutes, usually from 1 minute to 2 minutes. In such cases, the energy delivery will preferably be directed or limited so that tissue beyond that surrounding the renal pelvis, such as other renal structures including the papillae, the pyramids, and the like, is maintained below a temperature which would adversely affect the tissue function, typically below 45° C. A number of particular methods and devices for delivering energy to raise the tissue temperature are described in more detail below. In other embodiments, the energy exchange may comprise extracting energy from the tissue bed surrounding the blood vessels to cool said tissue bed to the temperature in the range from −10° C. to −100° C., typically from −50° C. to −100° C. Such cooling of the tissue will typically be carried out for a time period in the range from 3 sec. to 4 minutes, usually from 1 minute to 4 minutes. As with heating, preferred embodiments will also limit the cooling of tissue surrounding the renal pelvis to a temperature which will not adversely affect tissue function, typically above −10° C.

The effector may be advanced to the interior of the renal pelvis of the kidney in a variety of ways. Usually, the effector will be advanced through the urinary tract to reach the renal pelvis without the need to penetrate tissue. In such cases, the effector will be disposed on a urinary catheter, typically near a distal end of the catheter, and the urinary catheter will be advanced through the urethra, the bladder, and the ureter to reach the renal pelvis. Techniques for advancing catheters into the renal pelvis are known in the art, for example in connection with delivery of urinary stents to create drainage paths past urinary stones. Usually, an access or guide catheter and/or a guidewire will be placed through the urethra into the bladder to provide an access path to the os of the ureter at an upper end of the bladder. A second catheter carrying the effector will then be advanced through the access or guide catheter and/or over the guidewire and then through the length of the ureter so that the effector is position within the interior of the renal pelvis. The effector will usually be expanded and then be used to exchange energy and/or deliver active substances, as described in greater detail below.

Alternatively, the effector could be advanced to the renal pelvis percutaneously using known laparoscopic and endoscopic techniques. For example, an access trocar may be placed through the patient's abdomen, typically with insufflations of the abdomen to provide a working space. Usually, two, three or even four of such access penetrations will be formed, where one or more of these can be used to introduce the laparoscope or endoscope to visualize the kidney. Tools may then be advanced through others of the access ports in order to penetrate the retroperitoneal space and locate the kidney and to advance the effector through the retroperitoneal space, into the hilum of the kidney, and further into and on the renal pelvis. Once present in the renal pelvis, the effector will be used as described in more detail below in order to achieve the desired therapeutic effect.

A number of specific devices and methods may be employed using the effector in order to denervate, modulate, or inhibit the renal nerves within the wall of the pelvis or surrounding the renal pelvis. For example, the effector may comprise electrodes, typically on an inflatable or expandable structure, and the electrodes may be used to deliver radiofrequency energy across the wall of the renal pelvis to treat the nerves within the wall of the renal pelvis and/or further into the nerves surrounding the renal pelvis to heat the tissue bed surrounding the pelvis to treat the renal nerves. The electrodes may be monopolar, in which case the "active" electrodes on the effector will be connected to one pole of a radiofrequency generator while the other pole will be connected to a dispersive electrode placed on the patient's skin, typically on the small of the back. Alternatively, the radiofrequency electrodes could be bipolar, where one or more electrode pairs (nominally positive and negative) are disposed on the surface of the effector in order to deliver a more localized and higher current density to the tissue surrounding the renal pelvis to treat the nerves within the wall of the renal pelvis and/or further into the nerves surrounding the renal pelvis.

Alternatively, the effector may comprise an antenna to deliver microwave energy to heat the tissue within the wall of the renal pelvis and surrounding the renal pelvis, which includes the renal nerves and blood vessels. The microwave antenna may be disposed within the effector since it does not have to contact the tissue along the inner wall of the renal pelvis.

As a still further alternative, the effector may comprise an ultrasound transducer adapted to deliver ultrasound energy through the wall of the renal pelvis into the tissue bed surrounding the renal pelvis. For example, the ultrasound transducer may comprise an unfocused transducer array disposed over a surface continuous with a wall of the renal pelvis. Alternatively, the ultrasound transducer may comprise a high intensity focused ultrasound (HIFU) transducer array present on a structure or assembly within an interior portion of an expandable effector. In such cases, the expandable structure serves to position the ultrasound array relative to the tissue, and the ultrasound array can be arranged to deliver the energy in a direction selected to treat the target tissue bed and nerves. As a still further alternative, external transcutaneous ultrasound can be directed to the hilum and further into the renal pelvis. A target catheter may be placed through the urethra, bladder and ureter into the renal pelvis to help direct the treatment.

In a still further alternative, the effector may comprise a convective heat source in order to convectively deliver heat through the wall of the renal pelvis and into the tissue bed and nerves surrounding the pelvis. In a simple configuration, the convective heat source could be hot water or other heat exchange medium, heated either externally or more likely internally using, for example, an electrically resistive heat source.

In a still further example, the effector may comprise a convective cooling source in order to extract heat through a wall of the renal pelvis to cool the wall of the pelvis and the tissue bed surrounding the pelvis which contains the renal nerves and blood vessels. The cooling source may comprise a cryogenic fluid source with an expandable heat-exchanging effector positioned within the renal pelvis. Alternatively, the cooling source could rely on expanding a liquid or gas within the effector to achieve cooling.

In yet another example, the effector may comprise a cage or other support structure adapted to carry a radioactive or other radiation-emitting source. Useful radiation-emitting sources include radioactive "seeds," e.g., radioisotopes having short half-lives, as well as x-ray and other electronic radiation sources.

In a second aspect, apparatus and systems are presented for inhibiting, modulating, or destroying function of renal nerves in a patient's kidney. Apparatus comprise a shaft adapted to be introduced into an interior of the kidney, typically the renal pelvis, and an effector on the shaft to exchange energy and/or deliver an active substance from the interior of the kidney through a wall of the renal pelvis into the nerves within the wall of the renal pelvis surrounding the renal blood vessels in the kidney. The effector will typically comprise an expandable member which can be expanded within the renal pelvis to engage an interior wall of the renal pelvis, for example, comprising a compliant balloon or mechanically expandable cage adapted to inflate/expand to occupy all or a substantial portion of the interior volume of the renal pelvis. The compliant balloon or other expandable structure can thus serve to position elements of the effector against the interior wall of the renal pelvis and/or to locate an internal mechanism within the effector in a predetermined position/geometry relative to the wall and nerves of the renal pelvis. Usually, the effector will be adapted to limit the exchange of energy and/or the delivery of active substances into regions of the kidney beyond the renal pelvis, such as the papillae, the pyramids, the parenchyma, and other sensitive structures of the kidney which could be damaged by the protocols herein and adversely impact kidney function. While the inflatable body or other portions of the effector could engage such sensitive structures, the effector will be designed so that energy exchange and/or active substance delivery avoid such sensitive structures, for example by placing external elements on the effector away from such sensitive structures.

In a series of alternative embodiments, the effector may comprise an energy transfer structure on an external surface of the expandable member or other effector body. For example, the energy transfer structure located externally on the effector may comprise electrodes for delivering radiofrequency (RF) energy through the wall of the renal pelvis to the adjacent and surrounding renal nerves. Alternatively, the effector may comprise an energy delivery structure located internally to the effector, such as an antenna for delivering microwave energy through the wall and nerves of the renal pelvis to the surrounding renal nerves. Such internal energy delivery structures could also include ultrasound transducers for delivering ultrasound energy through the wall of the renal pelvis, for example high intensity focused ultrasound (HIFU) arrays. Still other internal energy delivery structures could comprise convective heat sources, including electrical resistance heaters, heated fluid exchange systems, and the like. Still other energy exchange structures include cryogenic other cooling structures, including both cryogenic fluid exchange structures and in situ cooling structures, such as gas expansion structures.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. Where applicable, some or all features may not be illustrated to assist in the description of underlying features. In the drawings:

FIGS. 7A-7D illustrate an energy delivery catheter having a plurality of tissue-penetrating electrodes which may be advanced into the wall of the renal pelvis adjacent to the ureteral os to deliver energy into the renal pelvis wall.

FIGS. 10A-10D illustrate an energy delivery catheter having a pair of malecots which may be opened to deploy wire electrodes in the renal pelvis adjacent to the ureteral os to deliver energy into the renal pelvis wall.

DETAILED DESCRIPTION OF ILLUSTRATIVE EMBODIMENTS

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

It is noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

Figure 1:
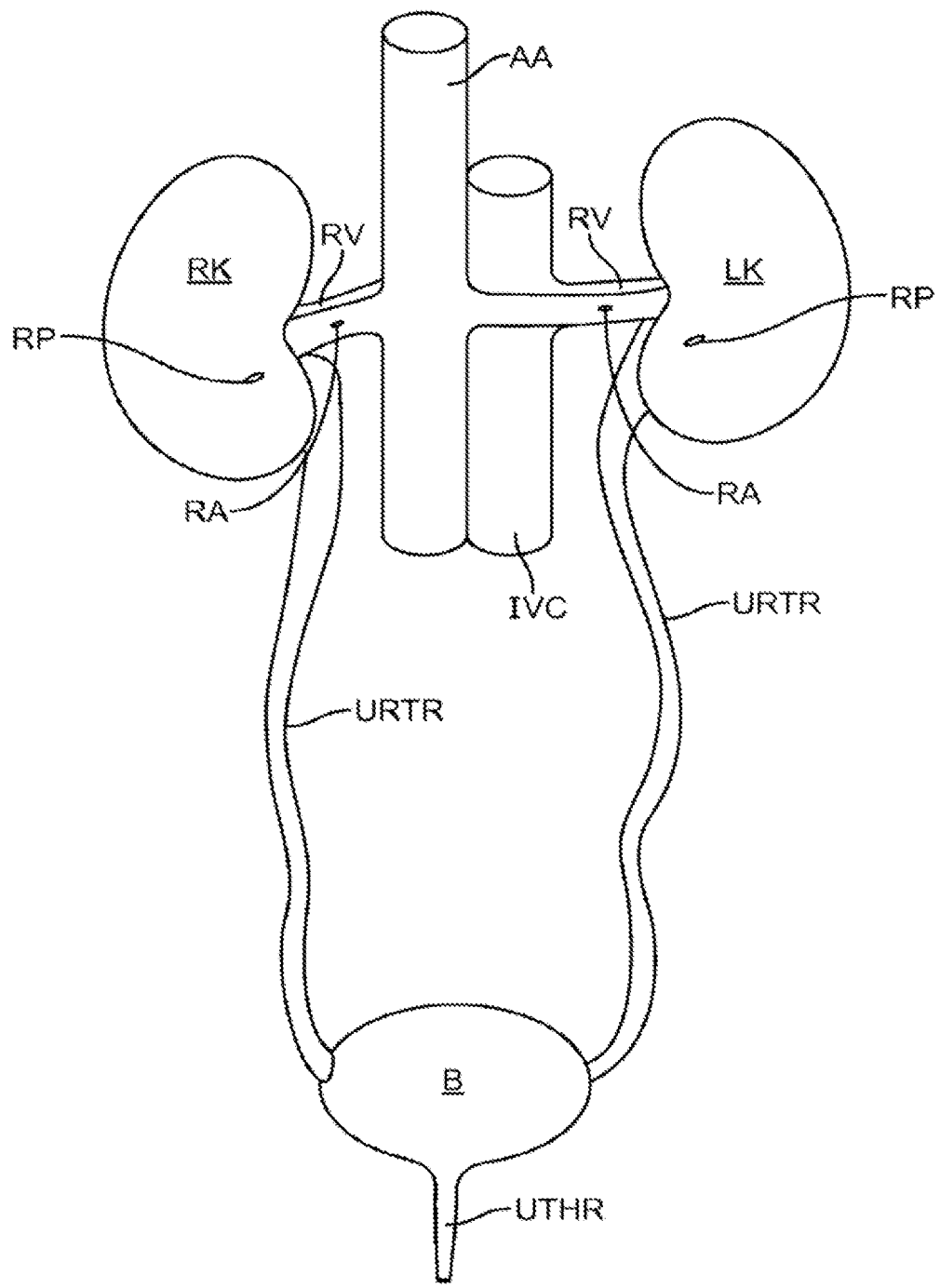
FIG. 1 is a diagrammatic illustration of a patient's urinary system.

A patient's urinary tract is diagrammatically illustrated in FIG. 1. The urinary tract includes the bladder B, which receives urine from the right and left kidneys RK and LK and drains the urine through the urethra UTHR. The kidneys each receive oxygenated blood through the renal artery RA from the abdominal aorta AA and blood from the kidneys is returned through the renal vein RV to the inferior vena cava IVC. Of particular interest to the present disclosure, the urine which is processed in the kidney is received in an interior cavity of each kidney referred to as the renal pelvis RP which acts as a funnel and delivers the urine into the top of the ureter URTR. Methods and protocols described herein will be performed within the interior of the renal pelvis RP in order to treat the renal nerves within the walls of the renal pelvis as well as the nerves surrounding the renal arteries within the adventitia and adipose tissue and to a lesser extent surrounding the renal veins which branch from the main renal artery and renal vein within the tissue of the kidney.

Figure 2B:
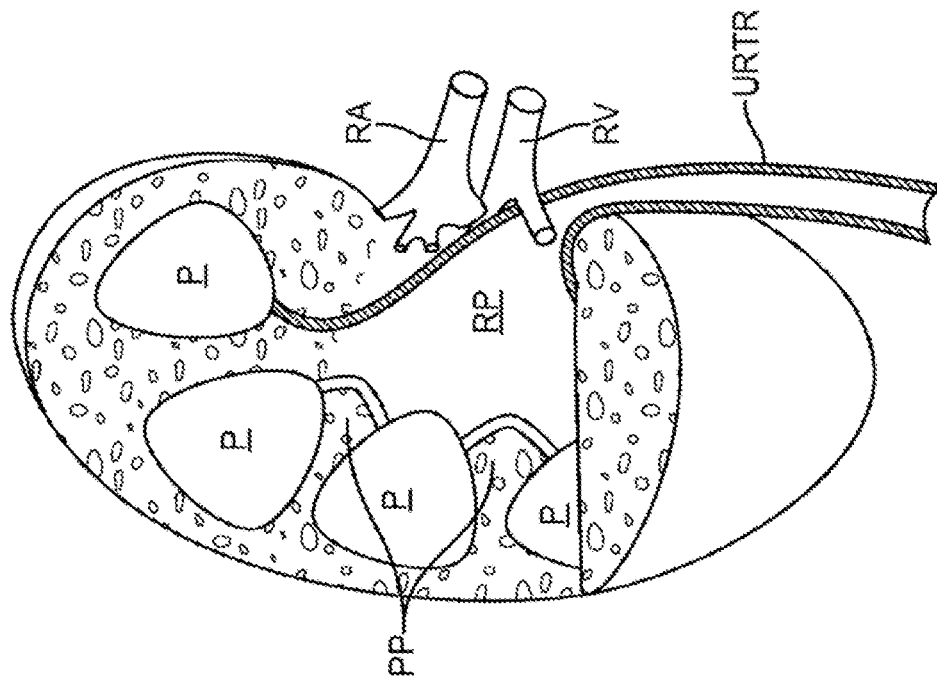
FIGS. 2A and 2B are partially broken-away illustrations of a patient's kidney showing the renal pelvis and other structures.
Figure 2A:
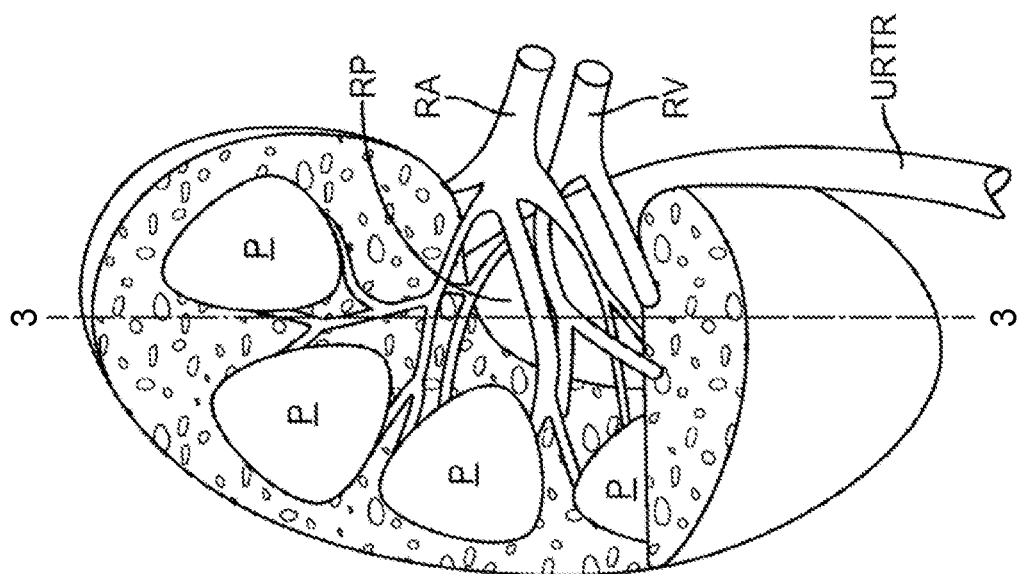

Referring now to FIGS. 2A and 2B, the right kidney RK is shown in section to expose the renal pelvis RP and other internal structures of the kidney. As shown in FIG. 2A, the renal pelvis is a funnel-shaped extension of the upper end of the ureter URTR and is surrounded by the branching portions of the renal artery RA and the renal vein RV, both of which branching structures extend into the body of the kidney and surround the pyramids P and other structures, including the papillae PP. The branching structures of the renal artery RA and renal vein RV as well as the anterior wall of the renal pelvis are removed in FIG. 2B to show the interior of the renal pelvis which is the target location for the therapies of several embodiments.

Figure 3:
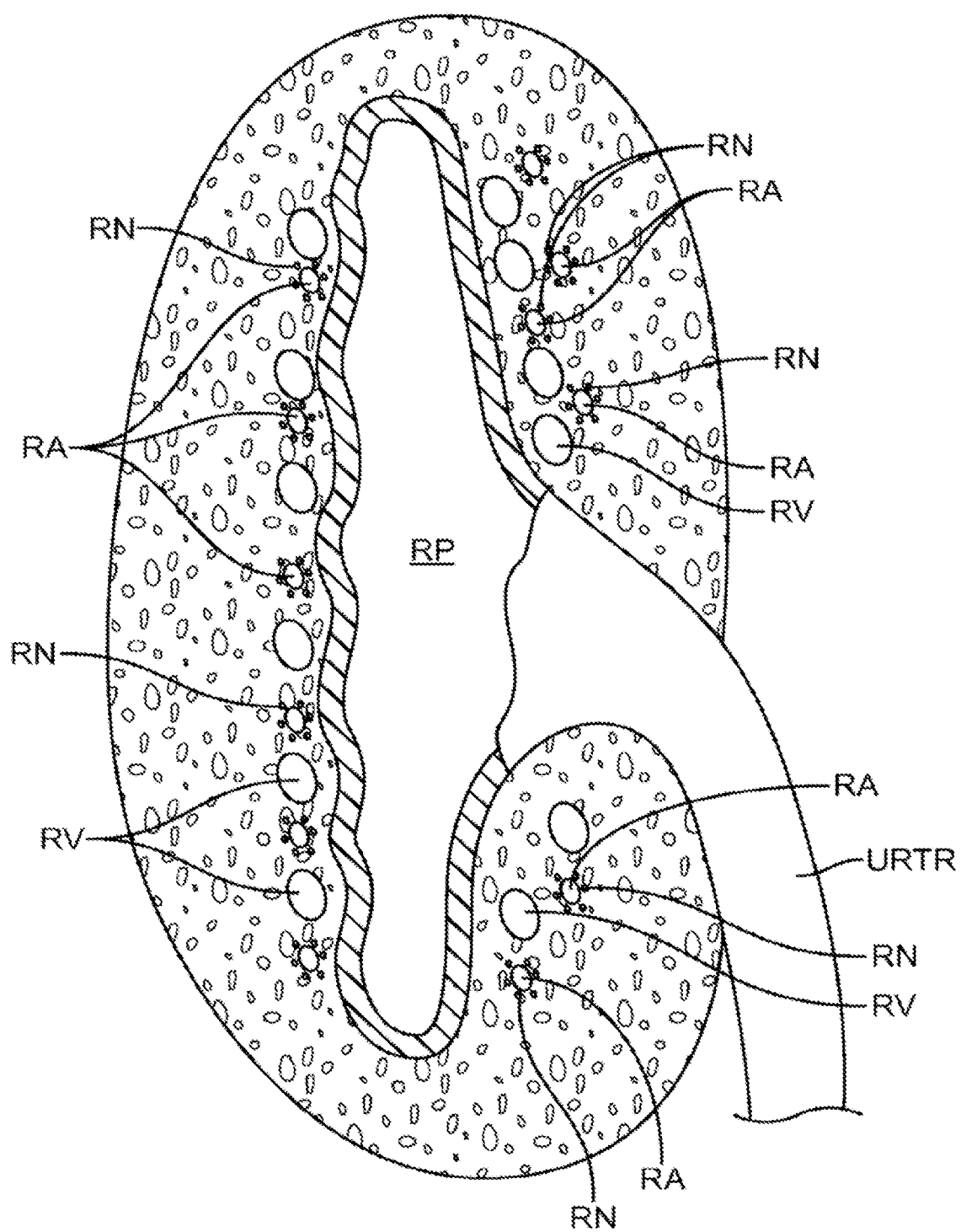
FIG. 3 is a cross-sectional view of the patient's kidney taken along line 3-3 of FIG. 2A.
Figure 3A:
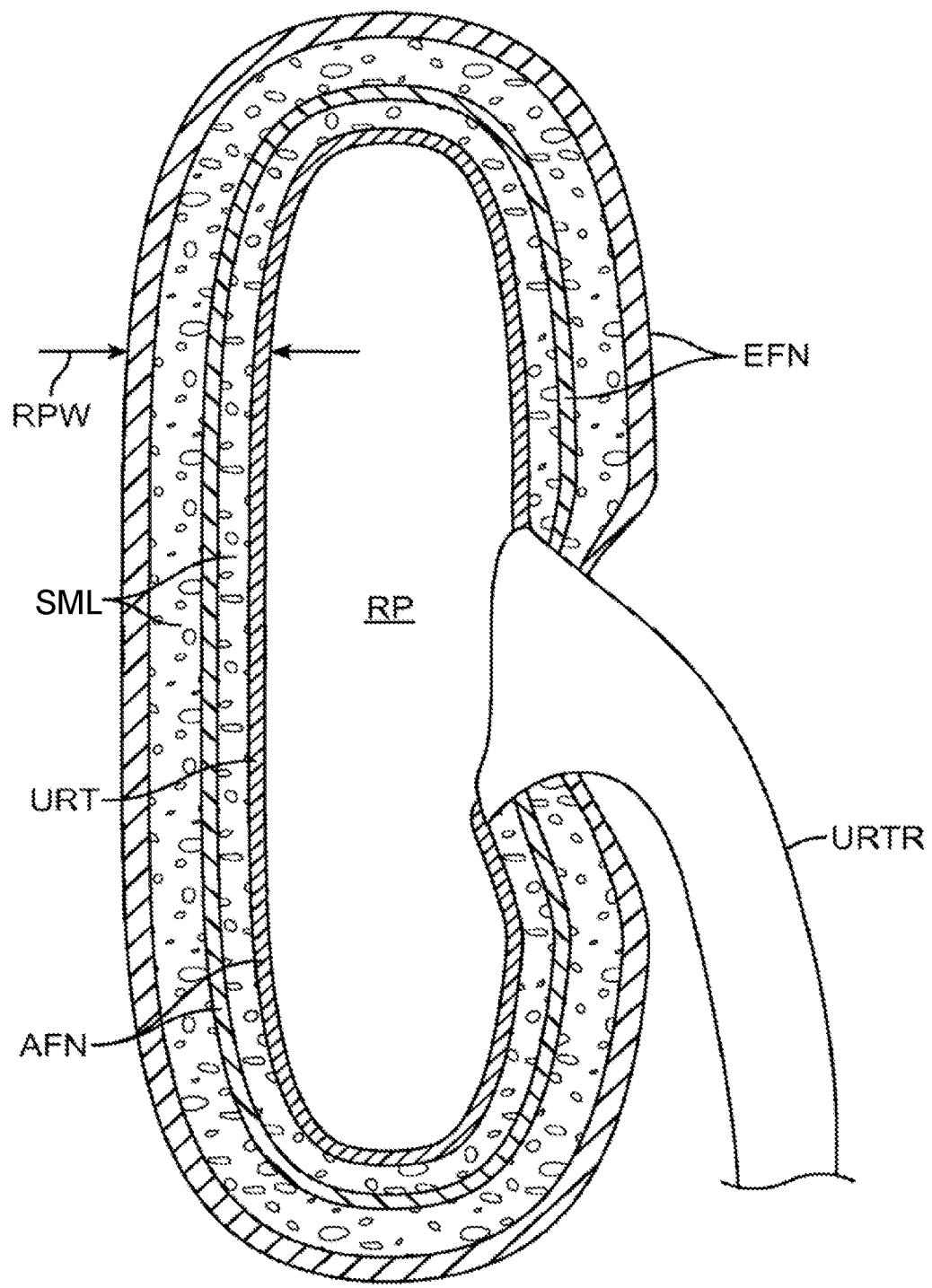
FIG. 3A shows the structure and location of renal nerves within the muscle layers, endothelium, and submucosa of the renal pelvis. The afferent nerves originate and are mostly contained within the wall of the renal pelvis. They have a direct effect on the efferent sympathetic nerves and are responsible for sympathetic muscle tone and vasoconstriction.

As further shown in FIG. 3 which is a cross-sectional view taken along line 3-3 of FIG. 2A, the renal nerves RN surround the renal blood vessels, particularly the renal arteries RA, extending adjacent to and surrounding the outer wall of the renal pelvis RP in a tissue bed surrounding the renal pelvis. As shown in FIG. 3A, the renal nerves follow the arteries and then divide. A portion of the divided nerves enter the renal pelvic wall RPW where they intertwine with the afferent nerves AFN that are located within the smooth muscle layers, endothelium and submucosa SML of the renal pelvis. The afferent nerves AFN originate and are mostly contained within an interior wall of the renal pelvis adjacent to the urothelium URT. The afferent nerves have a direct effect on the efferent sympathetic nerves EFN (which are generally located nearer the exterior surface of the renal pelvis wall RPW than are the afferent sensory nerves AFN) and are responsible for sympathetic muscle tone and vasoconstriction. It is the renal nerves shown in FIGS. 3 and 3A, and in particular the sensory afferent nerves AFN, which are typically but not exclusively the target structures to be treated by the methods and apparatus of several embodiments.

Figure 4A:
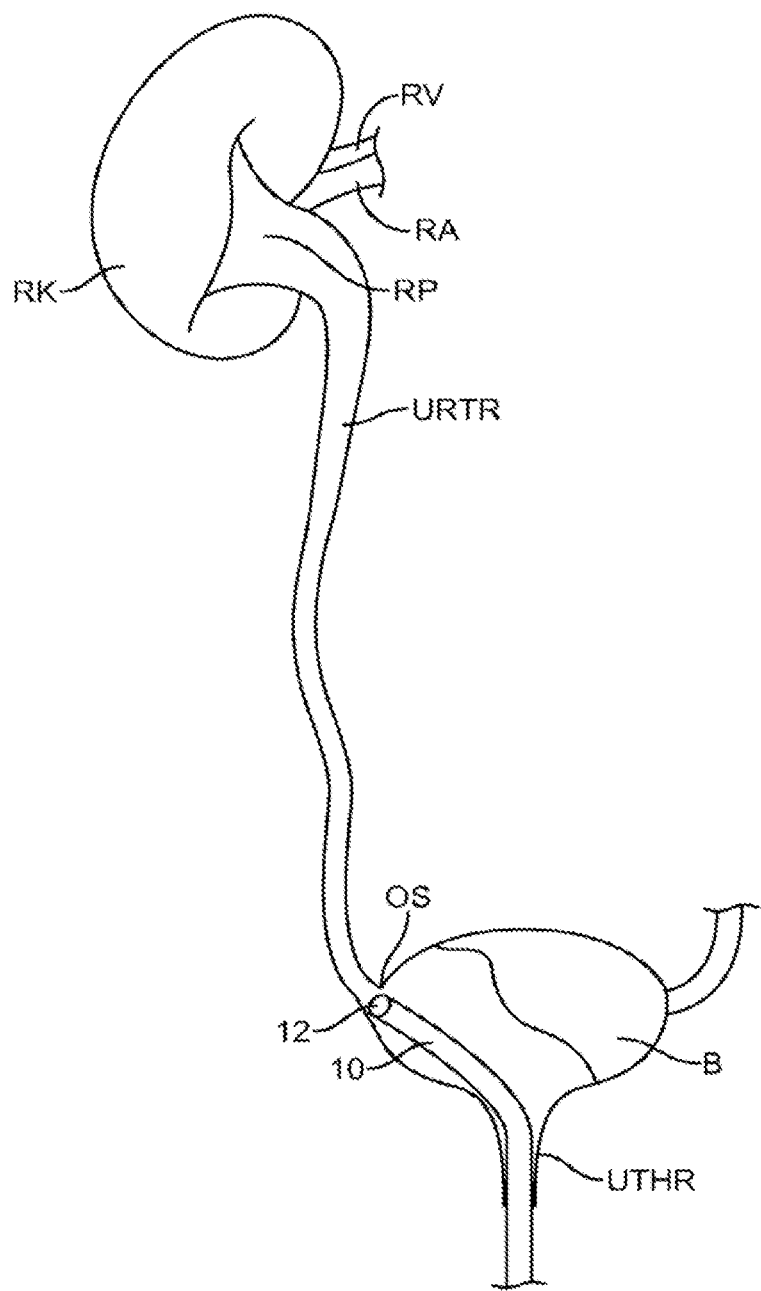
FIGS. 4A through 4C illustrate access and treatment of a patient's renal pelvis according to the principles of an embodiment.
Figure 4B:
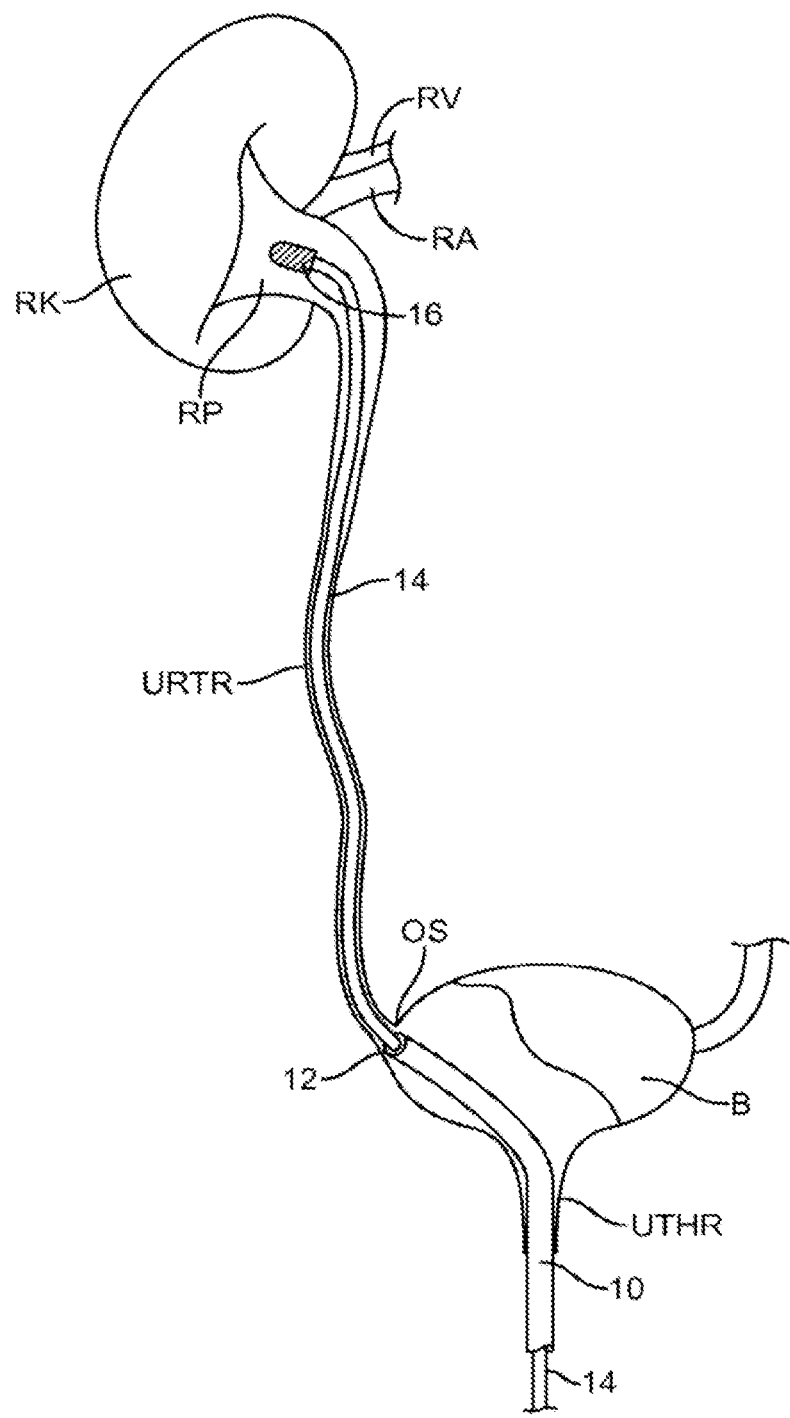
Figure 4C:
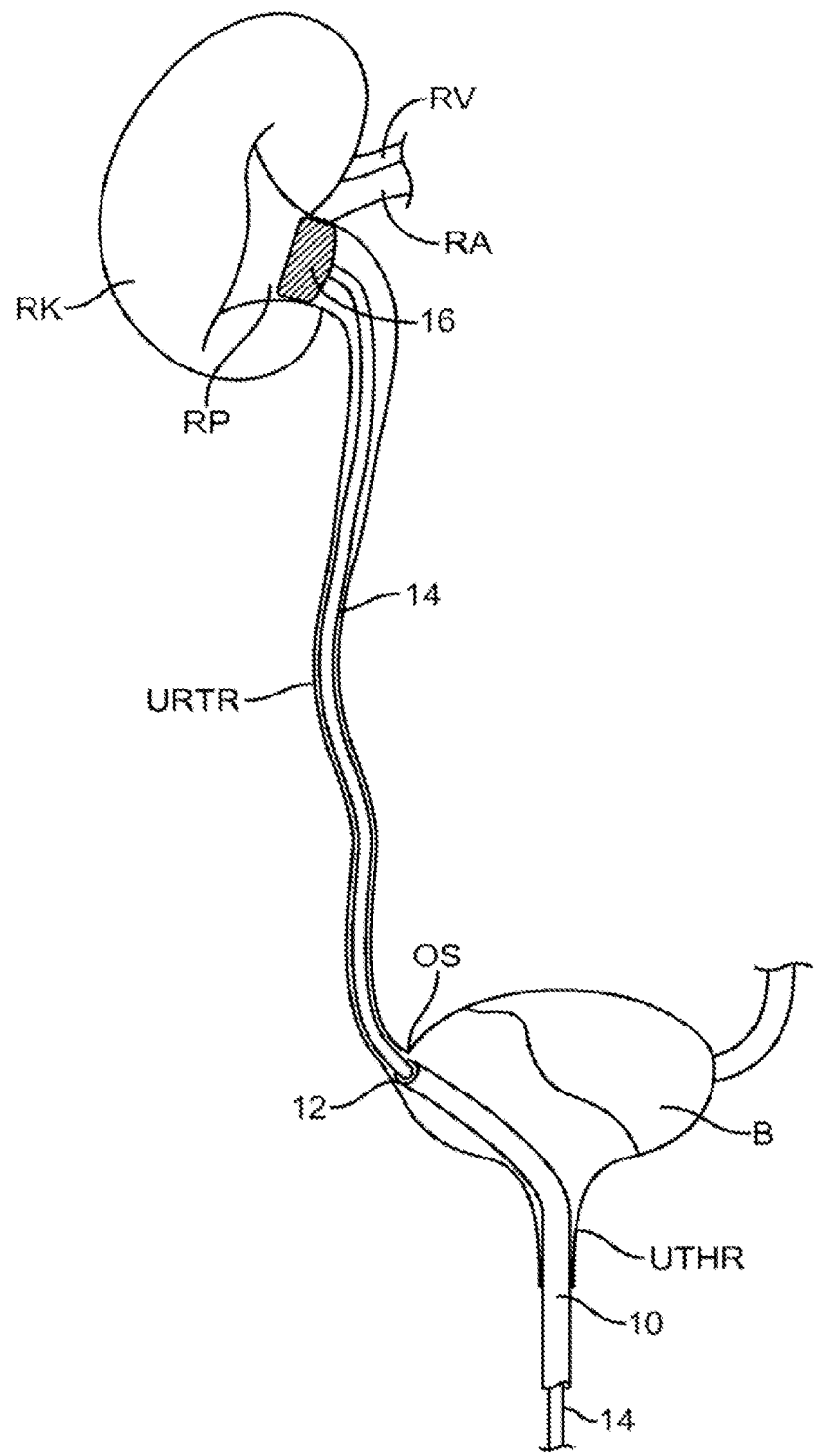

Referring now to FIGS. 4A through 4C, a first exemplary protocol for accessing and treating the renal nerves in the kidney will be described. Initially, a guide or other tubular catheter 10 is advanced through the urethra UTHR to position a distal port 12 adjacent the os OS at the lower end of the ureter URTR.

As shown in FIG. 4B, a treatment catheter 14 is then advanced through the guide catheter 1 (optionally over a guidewire), out of port 12, and into a lumen of the ureter URTR. An effector 16 at the distal end of the treatment catheter 14 is advanced into the renal pelvis RP, optionally under fluoroscopic and/or ultrasound guidance in a conventional manner.

Once in the renal pelvis RP, the effector 16 will be deployed in order to treat the renal nerves in accordance with the principles of the present disclosure. For example, the effector may comprise an expandable structure which is mechanically expanded or inflated within the renal pelvis to engage the interior walls of the pelvis as shown in FIG. 4C. Any one of a variety of energy exchange devices or substance delivery devices may then be employed to exchange energy or deliver the substances through the wall of the renal pelvis to treat the nerves embedded within the walls of the renal pelvis as well as the nerves embedded in the tissue surrounding the renal pelvis.

Figure 5A:
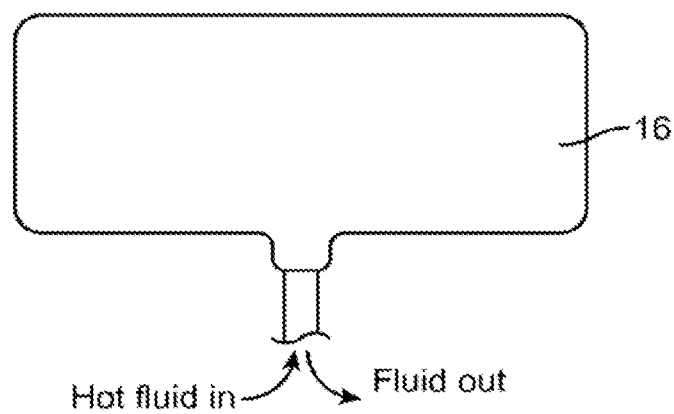
FIGS. 5A through 5F illustrate different effector designs that can be used for treating the renal nerves in accordance with the principles of the embodiments.
Figure 5B:
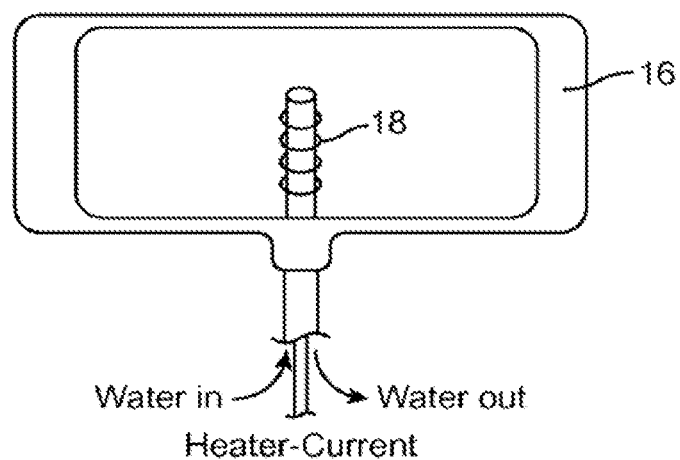

As shown in FIG. 5A, for example, the inflated or expanded effector 16 can be used to deliver convective heat through the wall of the renal pelvis, for example by delivering an externally heated fluid into the interior of the effector and removing the fluid from the interior to recirculate the hot fluid. As shown in FIG. 5B, it would also be possible to use an electrical resistance or other heater 18 which is positioned within the effector 16 in order to heat a fluid in situ where the fluid would not necessarily be recirculated. Typically, continuous irrigation will be provided through the catheter to cool the electrodes which in turn reduces damage to the adjacent tissue in contact with the electrode.

Figure 5C:
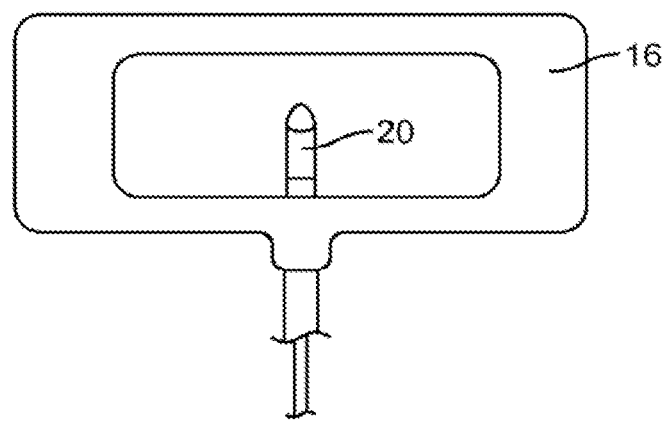

As shown in FIG. 5C, energy can be delivered in other ways, such as using a microwave antenna 20 which is positioned by the effector 16 to deliver microwave energy through the wall and into the nerves within the renal pelvis. Both the dimensions and geometry of the effector 16 as well as the transmission characteristics of the antenna 20 can be configured in order to selectively deliver the microwave energy into the tissue to achieve the targeted heating.

Figure 5D:
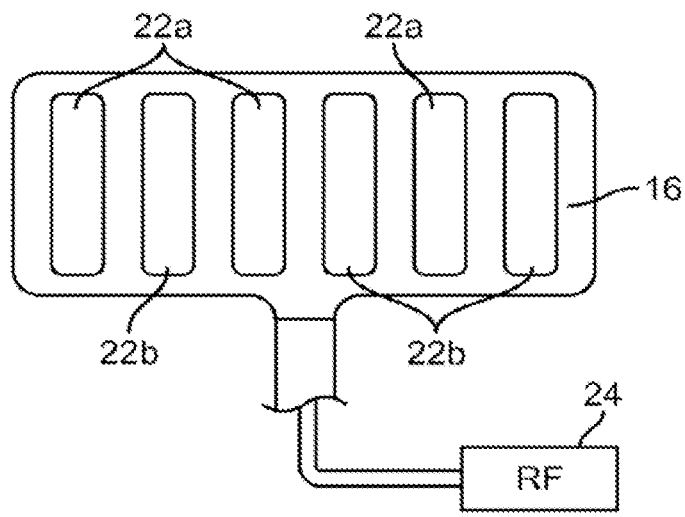

Still another alternative energy delivery mechanism is illustrated in FIG. 5D where bipolar electrodes 22a and 22b are arranged on the exterior of the effector 16 surface and connectible to an external radiofrequency generator 24 to deliver bipolar radiofrequency energy to the tissue. Again, the dimensions of the electrodes, spacing, and other system features can be selected to deliver energy to a proper depth in the wall of the renal pelvis as well as to the tissue beds surrounding the renal pelvis.

Figure 5E:
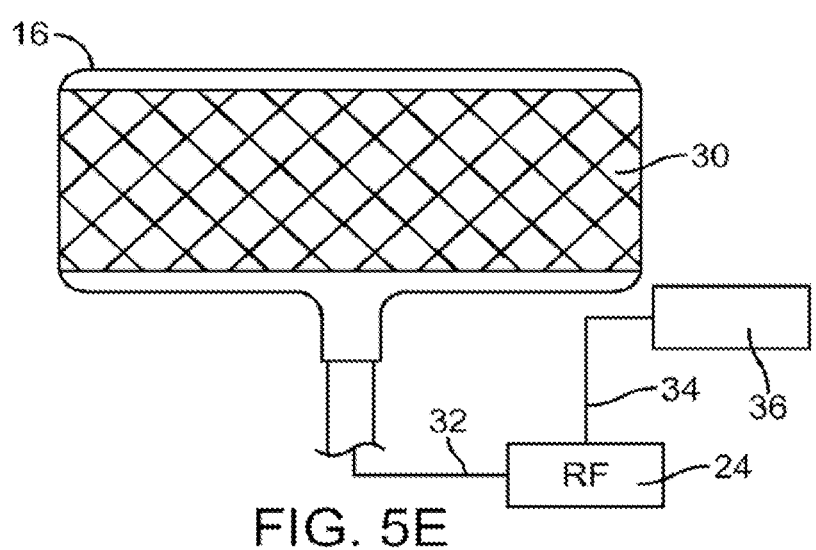

As shown in FIG. 5E, a single monopolar electrode 30 may be provided on the exterior of the effector 16 where one pole 32 of the RF generator 24 connected to the electrode on the effector and the other pole 34 connected to an external pad 36 which will be placed on the patient's skin, typically on the lower back.

Figure 5F:
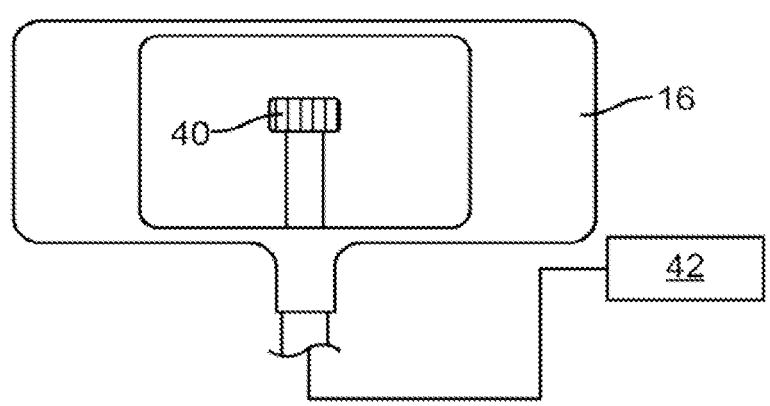

Still further, effector 16 construction shown in FIG. 5F includes an ultrasound phased array 40 positioned within the interior of the effector and connected to an external ultrasound generator 42. The ultrasound phased array 40 will typically be constructed to provide high intensity focused ultrasound (HIFU) in order to selectively deliver energy across the wall of the renal pelvis and into the tissue beds surrounding the pelvis in order to heat the tissue and treat the renal nerves in accordance with the principles of an embodiment.

Figure 6A:
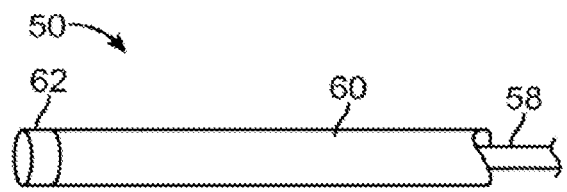
FIGS. 6A-6D illustrate an energy delivery catheter having an expandable cage which is deployed in the renal pelvis adjacent to the ureteral os to deliver energy into the renal pelvis wall.
Figure 6B:
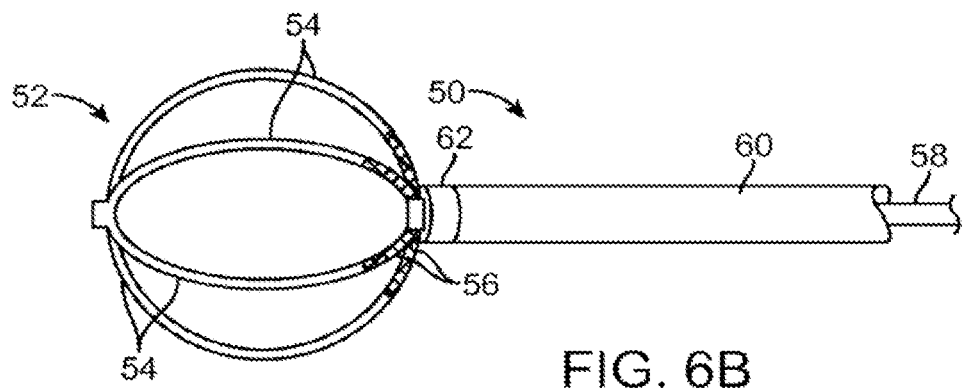
Figure 6C:
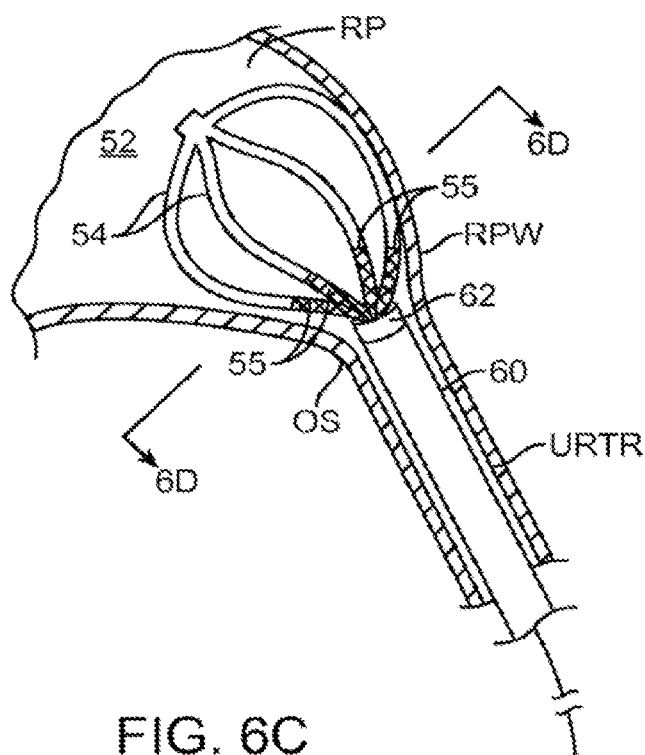
Figure 6D:
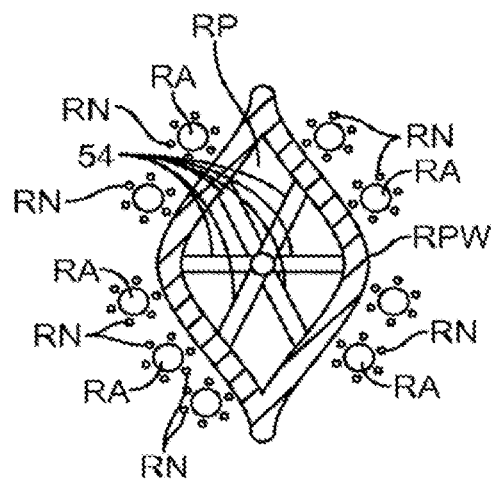

Referring now to FIGS. 6A-6D, an expandable catheter cage 50 comprises an expandable cage structure 52 including a plurality of electrode elements 54. The electrode elements will typically be formed from a shape memory alloy, such as nitinol, and will usually be electrically conductive along their entire lengths. A proximal portion of each electrode, however, will usually be covered with a layer of insulation 55 in order to inhibit energy delivery to the upper region of the ureter URTR through which the catheter is introduced. The catheter 50 further includes an inner shaft 58 and an outer sheath 60, where the outer sheath may be distally advanced over the expandable cage structure 52 in order to collapse the cage structure for delivery, as shown in FIG. 6A. By retracting the sheath 60 relative to the inner shaft 58, the cage 52 may be deployed as shown in FIG. 6B. After the catheter 50 is introduced through the ureter URTR, as shown in FIG. 6C, the sheath may be retracted in order to deploy the cage structure 52 within the renal pelvis RP adjacent to the ureteral os OS. The portions of the electrode elements 54 adjacent to the os will be insulated so that energy is preferentially delivered a short distance above the os in order to avoid damage to the ureter and other sensitive structures. The energy delivered through the electrode elements 54 will pass through the wall RPW of the renal pelvis in order to treat the renal nerves (RN), as shown in FIG. 6D. A radiopaque marker 62 can be provided at or near the distal end of the sheath 60 to assist in positioning the catheter 50 at or above the os under fluoroscopic imaging.

Referring now to FIGS. 7A-7D, a penetrating electrode catheter 70 includes a plurality of tissue-penetrating electrodes 72 deployed from an inner shaft 74 and having an outer sheath 76 reciprocally mounted thereover. The outer sheath 76 has a radiopaque marker 78 at its distal end (for positioning in the ureter URTR) and may be selectively retracted from a distal tip 80 of the inner shaft 74 in order to deploy the tissue-penetrating electrodes 72, as shown in FIG. 7B. Usually, the catheter 70 will have a port 82 opening to an inner lumen (not shown) to allow advancement over a guidewire GW, as shown in FIGS. 7A and 7C.

After the marker 78 of the catheter 70 is positioned at or just above the ureteral os OS, as shown in FIG. 7C, the inner shaft 74 may be advanced to deploy the electrodes 72 into the wall RPW of the renal pelvis RP. RF energy is then delivered from the power supply 84 in order to treat the renal nerves RN which surround the renal pelvis wall RPW as shown in FIG. 7D.

Figure 8A:
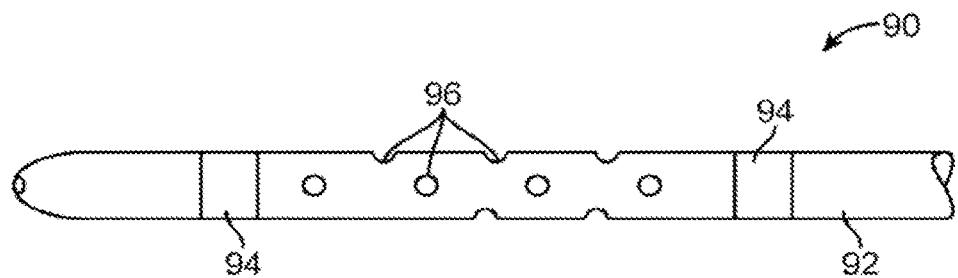
FIGS. 8A-8C illustrate an energy delivery catheter comprising a pair of bipolar electrodes and having vacuum ports to collapse the renal pelvis wall about the electrodes when the catheter is present in the renal pelvis adjacent to the ureteral os.
Figure 8B:
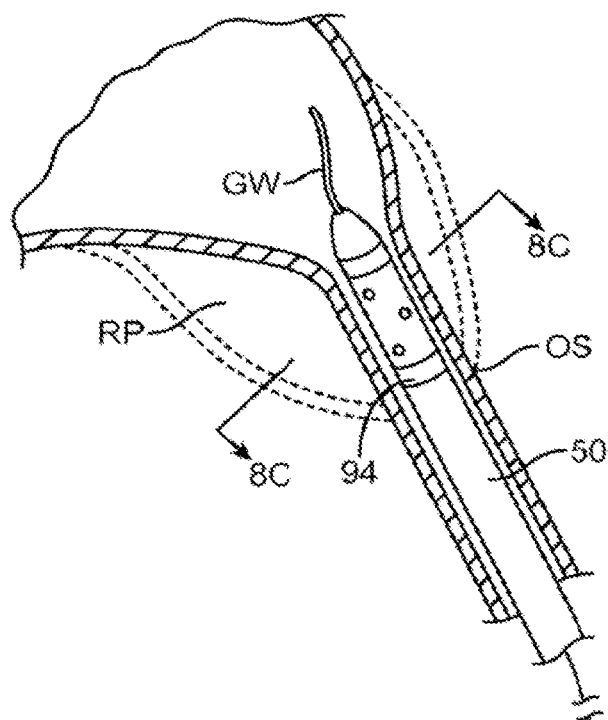
Figure 8C:
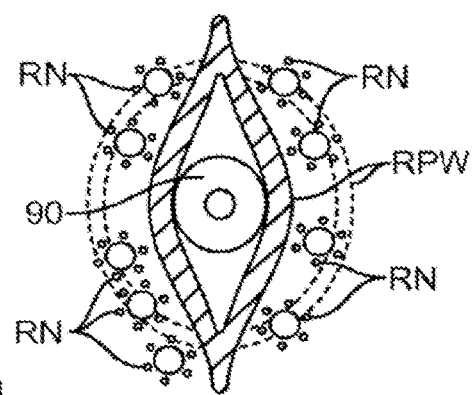

Referring to FIGS. 8A-8C, a bipolar electrode 90 having a pair of axially spaced-apart electrodes 94 comprises a catheter shaft 92 having a plurality of vacuum ports 96 disposed between the electrodes. The vacuum ports 96 communicate with an inner lumen (not illustrated) which allows a vacuum to be drawn through the ports in order to partially collapse the renal pelvis, as shown in FIGS. 8B and 8C. After the catheter 50 is advanced to a location where the proximal-most electrode 94 is advanced past the ureteral os OS, as shown in broken line in FIG. 8B, a vacuum may be drawn in the lower portion of the renal pelvis RP to collapse the walls, as shown in full line in both FIGS. 8B and 8C. An external power supply/controller 98 may include both a vacuum source and a radio frequency power source for connection to the catheter 90. After the wall of the renal pelvis is collapsed, radiofrequency energy will be delivered through the electrodes 94 from the power supply 98 in order to treat the renal nerves RN.

Figure 9A:
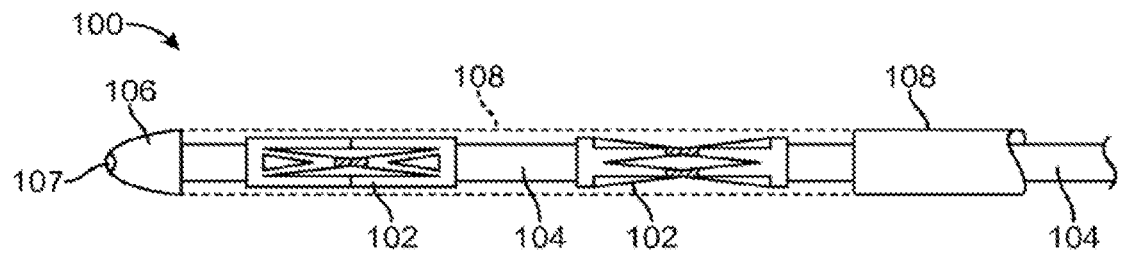
FIGS. 9A-9D illustrate an energy delivery catheter having a pair of expandable cages which may be deployed in the renal pelvis adjacent to the ureteral os to deliver energy into the renal pelvis wall.
Figure 9B:
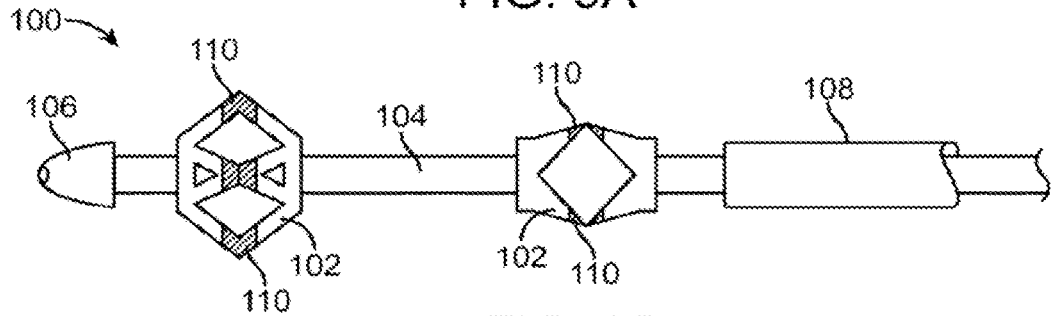
Figure 9C:
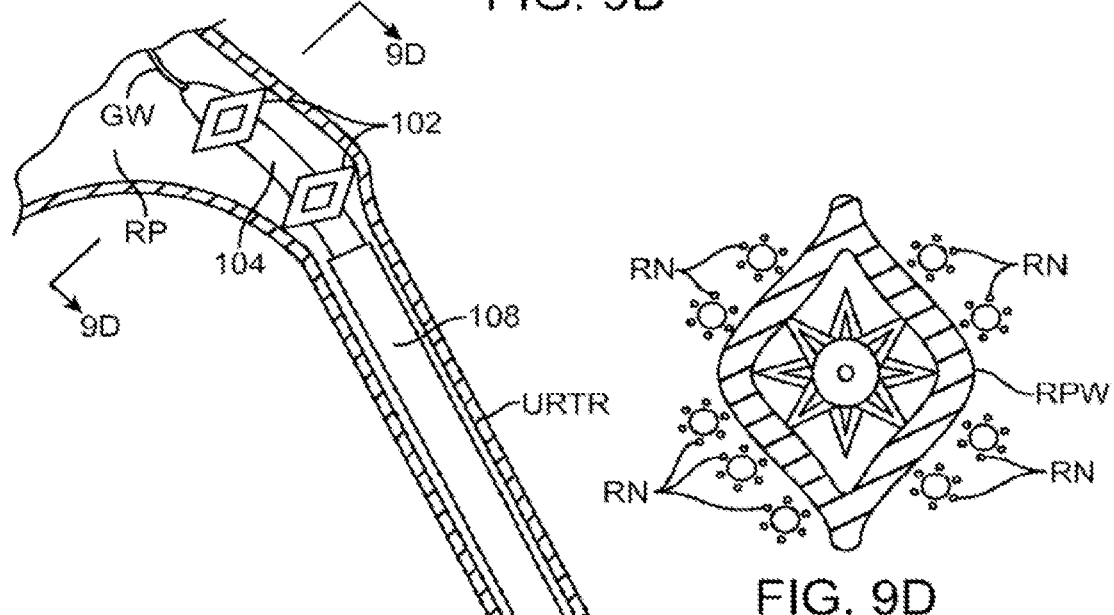
Figure 9D:
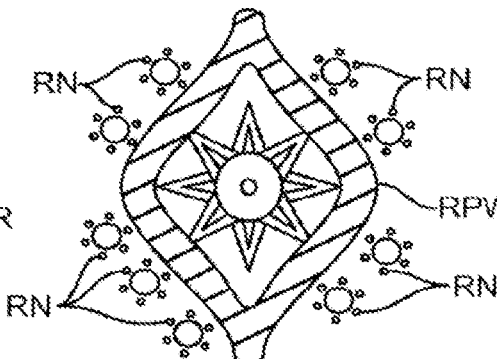

Further referring to FIGS. 9A-9D, a multiple cage catheter 100 has a plurality of individual cages 102 (with two cages illustrated) mounted on an inner shaft 104. The inner shaft terminates at a distal tip 106 having a port 107 which can receive a guidewire GW (FIG. 9A) through a central guidewire lumen (not illustrated). The cages 102 are self-expanding, typically being formed from nitinol or other electrically conductive shape memory material, and will be collapsed by an outer sheath 108 which may be advanced over the cages, as shown in broken line in FIG. 9A, or be retracted to allow the cages to expand as shown in full line in FIG. 9B. The catheter 100 may be advanced through the ureter URTR, as shown in FIG. 9C, where the sheath 108 is then retracted to allow the electrode cages 102 to expand and engage the wall of the renal pelvis RP, as shown in FIG. 9D. Each cage 102 will have a plurality of active electrode regions 110 which are usually formed by covering the non-active regions of the cage (i.e., everything except the active regions at the centers) with an insulating layer or material. After the cages 102 are deployed in contact with the inner surface of the renal pelvis wall RPW, radiofrequency energy may be delivered through power supply 112.

Referring now to FIGS. 10A-10D, a wire electrode catheter 120 comprises a catheter shaft 122 having a distal end 124. A first set of four axial slits 126a are circumferentially spaced-apart about the tubular wall of the catheter shaft 122, and a second set of four axial slits 126b are also circumferentially spaced apart about the catheter shaft at a region just proximal to the first set. Only four of the two slits 126a and two of the four slits 126b are visible with the remaining two of each set being hidden on the far side of the catheter shaft 122. By axially tensioning the catheter shaft 122, for example by pulling on a cable 127 which is attached at the distal end 124 of the shaft 122, the shaft may be foreshortened causing the sections between adjacent slits to project outwardly to form malecot structures 128, as best seen in FIG. 10B. Electrode wires 130 extend between the axially aligned sections of the first and second malecots so that the wires are advanced radially outwardly when the malecots are deployed by foreshortening the catheter shaft 122. The wires 132 are continuous and extend into an inner lumen of the shaft and exit the shaft at a proximal end thereof and are connected to a power supply 134.

In order to confirm proper deployment of the electrode wires 130, radiopaque markers 136 are formed distally to, between, and proximally to the slit-malecot structures 128, so that the markers will appear to move together under fluoroscopic observation as the malecots are deployed by pulling on cable 127.

As shown in FIG. 10C, the deployable structure of the catheter 120 is positioned just beyond the ureteral os OS to deploy the malecot structures 128 radially outwardly as shown best in FIG. 10D. The wires 130 between the malecots 128 will engage the walls of renal pelvis RP above the os OS, and energy may be applied from a power supply 134. Optionally thermocouples 132 will be formed at the radially outward tips of each malecot 128 such that they can penetrate the wall of the renal pelvis in order to monitor temperature during treatment. As before, energy will be delivered in order to inhibit or modulate the function of the renal nerves RN surrounding the renal pelvis wall RPW, as shown in FIG. 10D

EXPERIMENTAL

Background Endovascular renal denervation is known to produce useful blood pressure (BP) reductions. The data below demonstrate the safety and effectiveness of renal denervation by delivery of radiofrequency energy across the renal pelvis utilizing the natural orifice of the urethra and the ureters. This open-label, single-arm feasibility study enrolled patients with uncontrolled hypertension despite antihypertensive drug therapy. The primary effectiveness endpoint was the change in ambulatory daytime systolic BP (SBP) 2 months following renal pelvic denervation.

Surprisingly, the data further demonstrated a small but significant increase in eGFR and a significant decrease in mean serum creatinine, both of which correlate with a decreased risk of kidney disease and associated morbidities, including a reduced risk of stroke, congestive heart failure, and end-stage renal disease, as well as improved hormone function, including reductions in renin, aldosterone, and angiotensin.

Methods

Participants. Adults between the ages of 18 and 70 with uncontrolled hypertension were eligible for the study at either of two study sites. While continuing to take their background antihypertensive therapy of up to three antihypertensive medications, mean daytime systolic blood pressure measured by 24-hour ambulatory blood pressure monitoring (ABPM) was required to be at least 135 mm Hg and less than 170 mmHg, with mean daytime diastolic blood pressure less than 105 mm Hg. For those not receiving medications, mean daytime systolic blood pressure was required to be at least 140 mm Hg and less than 170, with mean daytime diastolic blood pressure less than 105 mm Hg. However, while the protocol allowed for participation of both on-med and off-med patients, a decision was made early during the patient enrollment period to recruit only those patients receiving antihypertensive medications. This study report is based on the 18 patients on antihypertensive drug therapy.

Exclusion criteria included an estimated glomerular filtration rate (eGFR) under 45 mL/min/1.73 m$^2$ (calculated via the CKD-EPI Creatinine Equation, National Kidney Foundation), type I diabetes, clinically significant structural heart disease and secondary hypertension. The study (NCT05440513) was approved by the local Ethics Committee. Written informed consent was obtained from all patients before study enrollment.

Study Procedures. Baseline evaluation included measurement of automated office blood pressure and 24-hour ambulatory blood pressure monitoring along with laboratory assessment of serum and urine parameters according to a standard routine. Following collection of blood and urine specimens, patients were seated and allowed to rest for 5 minutes prior to use of an automated blood pressure measurement device (HEM-907XL, Omron Healthcare, Bannockburn, IL) which recorded blood pressure in each arm. Office blood pressure measurement was recorded in triplicate with one-minute separations between measurements. The arm with higher blood pressure at the baseline assessment was used for all subsequent measures. Study personnel would then witness the antihypertensive medication self-administration before positioning the arm cuff for ambulatory blood pressure monitoring (ABP OnTrak 90227, Spacelabs Healthcare, Snoqualmie, WA) on the same arm as used for office blood pressure measurements. Blood pressure was measured every 20 minutes during the day (0600-2159 h) and every 30 minutes at night (2200-0559 h). Patients would return the following day, at a time to assure at least 24 hours of blood pressure recording time, for the device to be removed. Additional baseline assessments included a pregnancy test where relevant, electrocardiogram, echocardiogram, computed tomographic (CT) urography and renal ultrasound.

For those patients meeting entry criteria, renal pelvic denervation was performed via the use of the Verve Medical Phoenix™ system. (Verve Medical, Paradise Valley, AZ). This system includes an RF generator and monopolar ablation device with 4 spherical electrodes. A dispersive electrical grounding pad was used (Universal Electrosurgical Pad with Cord, REF 9135-LP, 3M, Saint Paul, MN). The ablation device is placed into the renal pelvis following insertion of a 0.035"-0.038" soft tip guidewire into the bladder under visual guidance via rigid cystoscope, which is then advanced under fluoroscopy past the ureteropelvic junction. A sheath (Destina™ Twist, Oscor, Inc., Palm Harbor, FL) is passed over that wire to allow for placement of the Phoenix™ ablation device into the pelvis, beyond the ureteropelvic junction. The generator delivers up to 30 watts of power via this ablation device, which has 4 spherical conductors on a nitinol helix designed to expand into the renal pelvis and abut the uroepithelial lining. When activated, energy is delivered to increase the temperature to 60° C. within 20 seconds and maintain 60° C. for 2 minutes. Energy is delivered for a single cycle, then repeated in the other kidney. At the completion of the ablation, physicians were permitted to place ureteral stents at their discretion, which, when deployed, remained in place until the day 14 visit.

Unless clinically necessary, physicians and subjects were encouraged not to terminate or add antihypertensive medications following renal pelvic denervation until completing the Month 2 assessments, with addition of medicines permitted thereafter if office blood pressure continued to be uncontrolled. Post-treatment assessments were scheduled for Day 1, Day 14 and Month 1 with primary endpoints of safety and effectiveness performed at Month 2. At each visit, subjects underwent clinical evaluation including pain assessment and office blood pressure measurement.

At Day 14, Month 1 and Month 2, specimens were obtained for blood and urine testing. At Month 1 and 2, Ambulatory blood pressure monitoring was performed. At Month 1, renal ultrasound and CT urography were repeated. Concomitant medications were recorded, and adverse events were elicited at every visit.

Safety events of interest were defined in the protocol as: cardiovascular (including acute coronary syndrome, stroke, acute kidney injury, or death), device and procedure-related adverse events, urologic events (i.e., infections, hematuria, pain, urinary incontinency and/or obstruction within 14 days of the procedure) and clinically significant changes in serum and urine biochemistry.

Statistical Analysis.

The objectives of the study were to assess the safety and effectiveness of the Verve Medical Phoenix™ system. Safety was assessed through laboratory, urologic imaging and clinical events, included adverse events, serious adverse events and treatment-emergent adverse events.

The primary effectiveness endpoint was the mean change in daytime systolic blood pressure measured by ABPM from baseline to 2 months. Additional endpoints included changes in 24-hour ambulatory blood pressure monitoring and office blood pressure.

Summary single timepoint measurements and baseline characteristics are expressed as mean±SD (standard deviation) or percentages (%). Changes in continuous variables from baseline are shown as mean difference with 95% confidence intervals (CI). P values for individual time points are based on paired t-tests with changes through the assessment at Month 2, the primary endpoint, are based of mixed models (i.e., random effects models) using the Satterthwaite approximation for degrees of freedom for the overall p-value (F-statistic) and confidence intervals (t-statistic). Statistical analysis was performed using R version 4.1.3 (R Core Team 2022). A value of $p<0.05$ was considered significant. Subgroup analyses considered a $p<0.10$ as significant. DH had full access to all data from the clinical trial and was responsible for the integrity of the data used in the analysis.

Results

Eighteen patients (mean age 56±12 years) were enrolled on average antihypertensive drug intake of 2.7 daily. Renal pelvic denervation reduced mean daytime SBP by 19.4 mmHg (95% CI: −24.9, −14.0, $p<0.001$) from its baseline of 148.4±8.7 mm Hg. Mean nighttime (−21.4 mmHg, 95% CI: −29.5, −13.3) and 24-hour (−20.3 mmHg, 95% CI: −26.2, −14.5) SBP fell significantly ($p<0.001$) as did the corresponding diastolic BP (DBP) ($p<0.001$). Office SBP decreased from 156.5±12.3 mmHg by 8.3 mmHg (95% CI: −13.2, −3.5, p=0.002) within 24 hours post-procedure and by 22.4 mmHg (95% CI: −31.5, −13.3, $p<0.001$) by 2 months. Office DBP was reduced (p=0.001) by 2 months. Mild transitory back pain followed the procedure, but there were no serious adverse events. Serum creatinine decreased by 0.08 mg/dL (p=0.02) and estimated glomerular filtration rate increased by 7.2 mL/min/1.73 m$^2$ (p=0.03) 2 months following ablation procedure.

Figure 11:
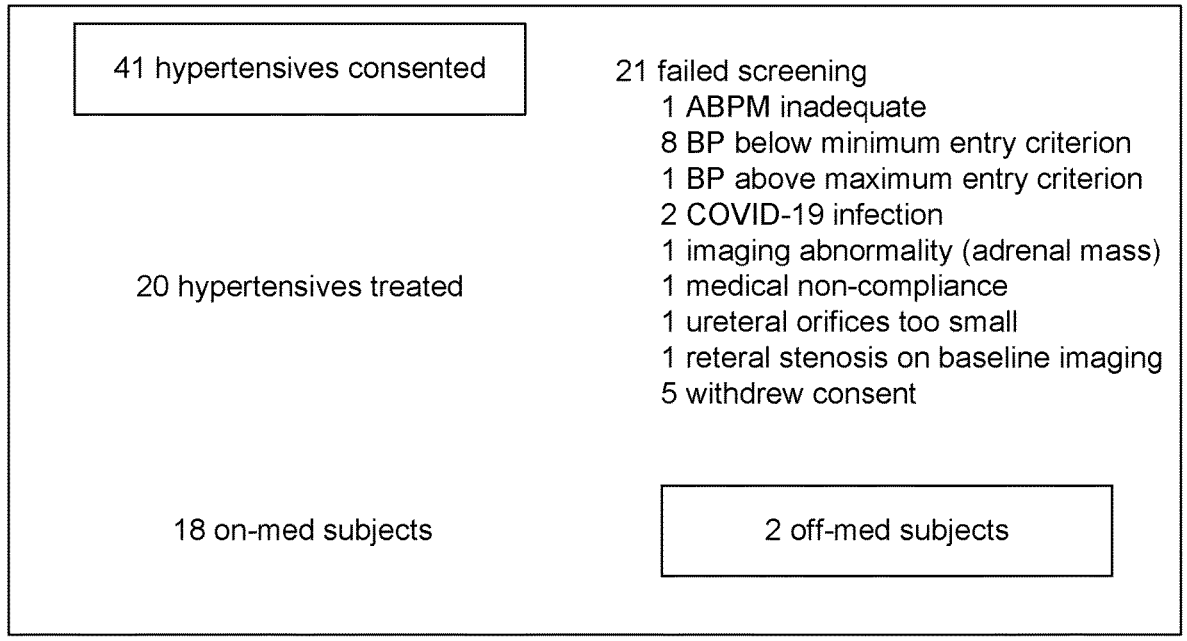
FIG. 11 is a consort diagram.

Baseline. Of 41 patients who signed informed consents, 21 were excluded (FIG. 11) including ten who were disqualified for failing to meet the study's blood pressure entry criteria, two due to COVID-19 infection, one identified with ureteral stenosis on baseline imaging, and one with ureteral orifice too narrow to allow for the sheath to be advanced, in whom the option of pre-stenting to enable performance of renal pelvic denervation 1-2 weeks later in this latter case was not employed.

The study population included 18 patients receiving antihypertensive medicines (Table 1) and two not receiving blood pressure lowering drugs, with the focus of this report on those patients receiving antihypertensive therapy. Average age was 56±12 years, the cohort included 7 women and 11 men who, on average, were treated with 2.7 antihypertensive drugs (Table 1).

TABLE 1

Select baseline characteristics of on-med subjects (n {%}, mean (SD))

| Characteristic | n = 18 |
|---|---|
| Age | 56 (12) |
| Female subjects | 7 (39%) |
| Body mass index (m/kg$^2$) | 31.6 (4.5) |
| Diabetes mellitus | 3 (17%) |
| Myocardial infarction | 2 (11%) |
| Coronary artery disease | 3 (17%) |
| estimated Glomerular Filtration Rate (ml/min/1.73 m$^2$) | 80 (18) |
| Number of hypertension drugs | 2.7 (0.5) |
| Angiotensin converting enzyme inhibitor | 16 (89%,) |
| Angiotensin receptor blocker | 1 (5.6%) |
| Calcium channel blocker | 14 (78%) |
| Beta-blocker | 7 (39%) |
| Diuretic | 10 (56%) |
| Oral diabetic | 3 (17%) |
| Statin | 10 (56%) |

Procedural Safety. No serious intra-procedural adverse events were observed. Following renal pelvic denervation, bilateral double-J ureteral stents were placed at investigators' discretion in 9 of 18 patients, which were removed in the office at the 14-day follow-up without complication.

Adverse Events. There were no serious adverse events and no treatment-emergent adverse events. In those subjects without stent placement, 5/9 reported back/flank pain, while 7/9 who had stents placed reported some pain or discomfort. By day 14, none of the nine patients without stents had pain while 3 patients with stents in place reported mild back or flank pain that persisted following hospital discharge but which resolved prior to or one day following removal of the stents (with average pain score of 3 out of 10 at day 14). In one subject, a renal stone 2.5-3 mm was evident one month after treatment, in whom the baseline study showed evidence of microliths and calcifications, indicating stone formation prior to treatment. The site reported that there was no stone evident on ultrasound imaging at month 6 or month 12. The one subject with proteinuria on a scheduled urinalysis had repeat study 4 days later with no evidence of proteinuria. There were no interventions or concomitant therapies for either of these two patients, and both were categorized as mild and resolved. Nonetheless, the investigator listed these as adverse events. One patient's hemoglobin level dropped from 11.6 g/dL at baseline to 9.8 g/dL at month 1 with initiation of iron anemia at month 6 follow-up. No adverse events are ongoing (Table 2).

TABLE 2

Safety and tolerability of renal pelvic denervation.

| Event | n (%) |
|---|---|
| Post-procedure back/flank pain* | 12 (67%) |
| Persistent back/flank pain | 0 (0%) |
| Urinary tract infection† | 2 (11%) |
| Cystitis | 0 (0%) |
| Proteinuria | 1 (6%) |
| Anemia | 1 (6%) |
| Renal stone | 1 (6%) |
| Perforation | 0 (0%) |
| Hypertensive crisis | 0 (0%) |
| Acute kidney injury | 0 (0%) |
| Renal failure | 0 (0%) |
| Acute coronary syndrome | 0 (0%) |
| Stroke | 0 (0%) |
| Hospitalization | 0 (0%) |
| Death | 0 (0%) |
| Treatment-emergent adverse event | 0 (0%) |
| Serious adverse event | 0 (0%) |

*Post procedure back/flank pain was evident by day 14 only in 3 subjects - each of whom had stents in place - with average score of 3 out of 10, with pain resolved within 1 day of stent removal.
†Both urinary tract infections responded to treatment with oral antibiotics.

Figure 12A:
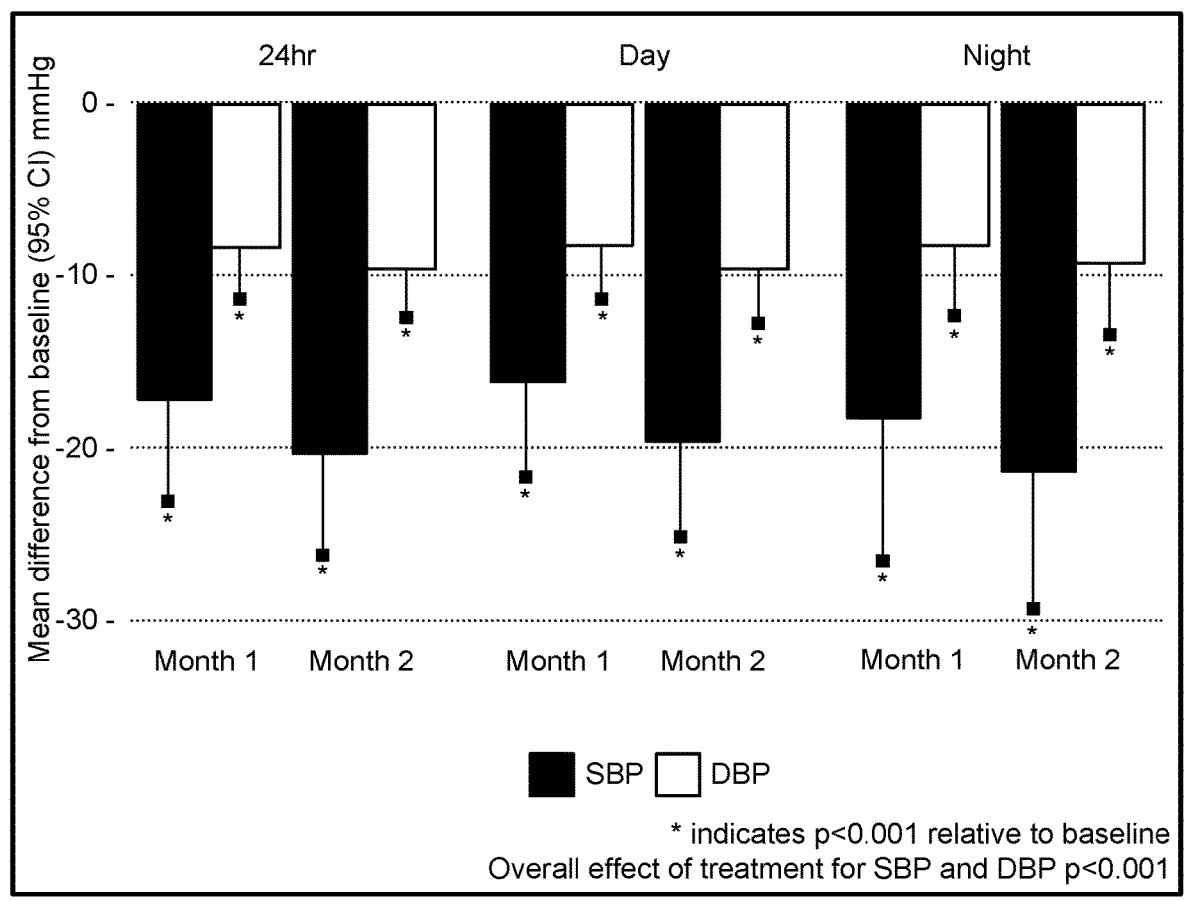
FIGS. 12A and 12B are bar charts showing the effect of renal pelvic denervation on ambulatory blood pressure reflected by (a) changes 1 and 2 months after ablation (* indicates p<0.001 by t-test, overall effects for changes in systolic blood pressure (SBP) and diastolic blood pressure (DBP) through Month 2 by linear mixed model at p<0.001) with (b) persistent 24-hour effects on SBP and DBP from baseline to month 2 (means with standard errors calculated by averaging all blood pressures taken during that hour).
Figure 12B:
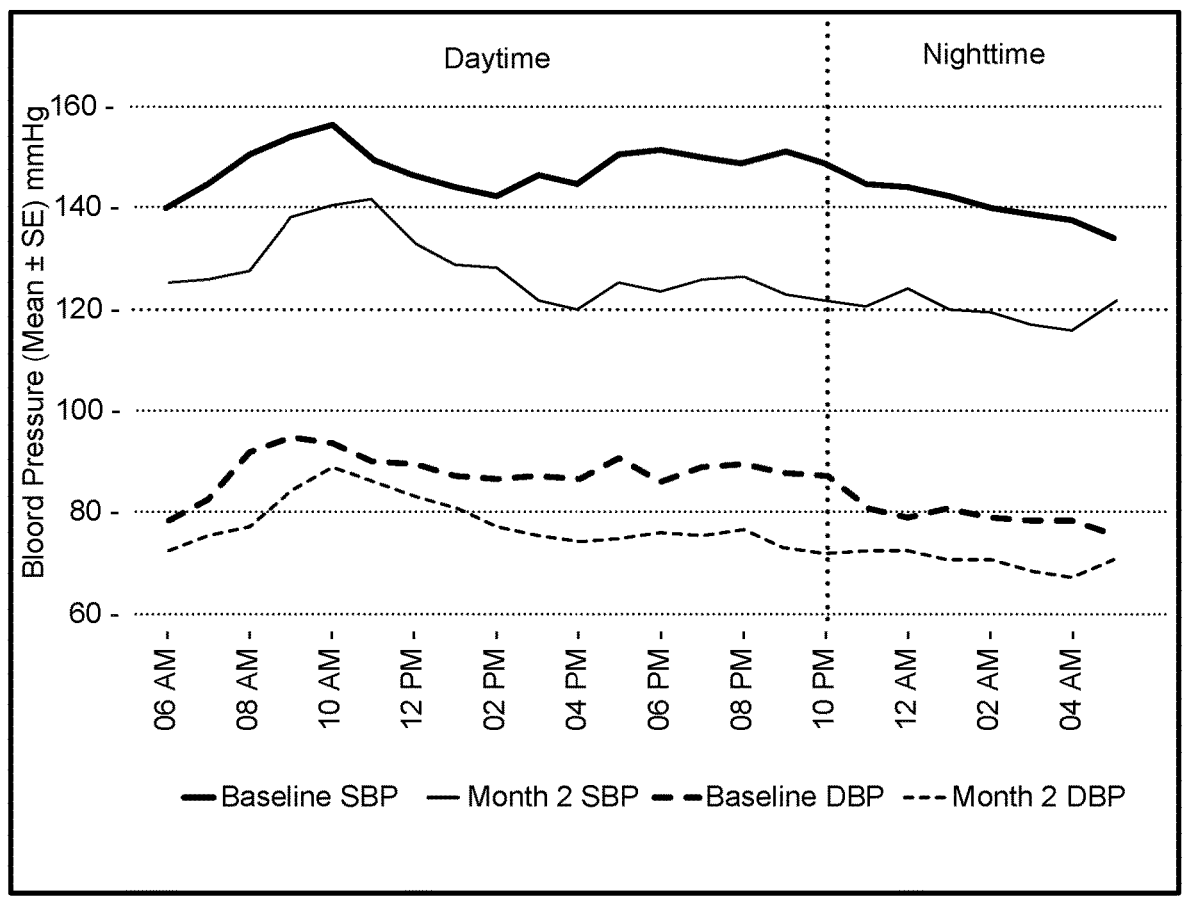

Effect on Blood Pressure. The primary effectiveness endpoint of daytime systolic blood pressure at 2 months post-procedure was significantly reduced by 19.4 mm Hg (95% CI: −24.9, −14.0, p<0.001). There were also significant reductions in mean 24-hour systolic blood pressure by 20.3 mm Hg (95% CI: −26.2, −14.5, p<0.001) and nighttime systolic blood pressure by 21.4 mm Hg (95% CI: −29.5, −13.3, p<0.001). The corresponding changes for diastolic blood pressure were 9.7 mm Hg daytime (95% CI: −12.7, −6.8), −9.2 mm Hg nighttime (95% CI: −13.3, −5.0), and 9.6 mm Hg over 24 hours (95% CI: −12.5, −6.6). All these diastolic blood pressure changes were significant (p<0.001). (FIG. 12A) The changes in ambulatory blood pressure over 2 months following renal pelvic denervation are evident over 24 hours, including an effect during the morning blood pressure surge. (FIG. 12B)

Figure 13:
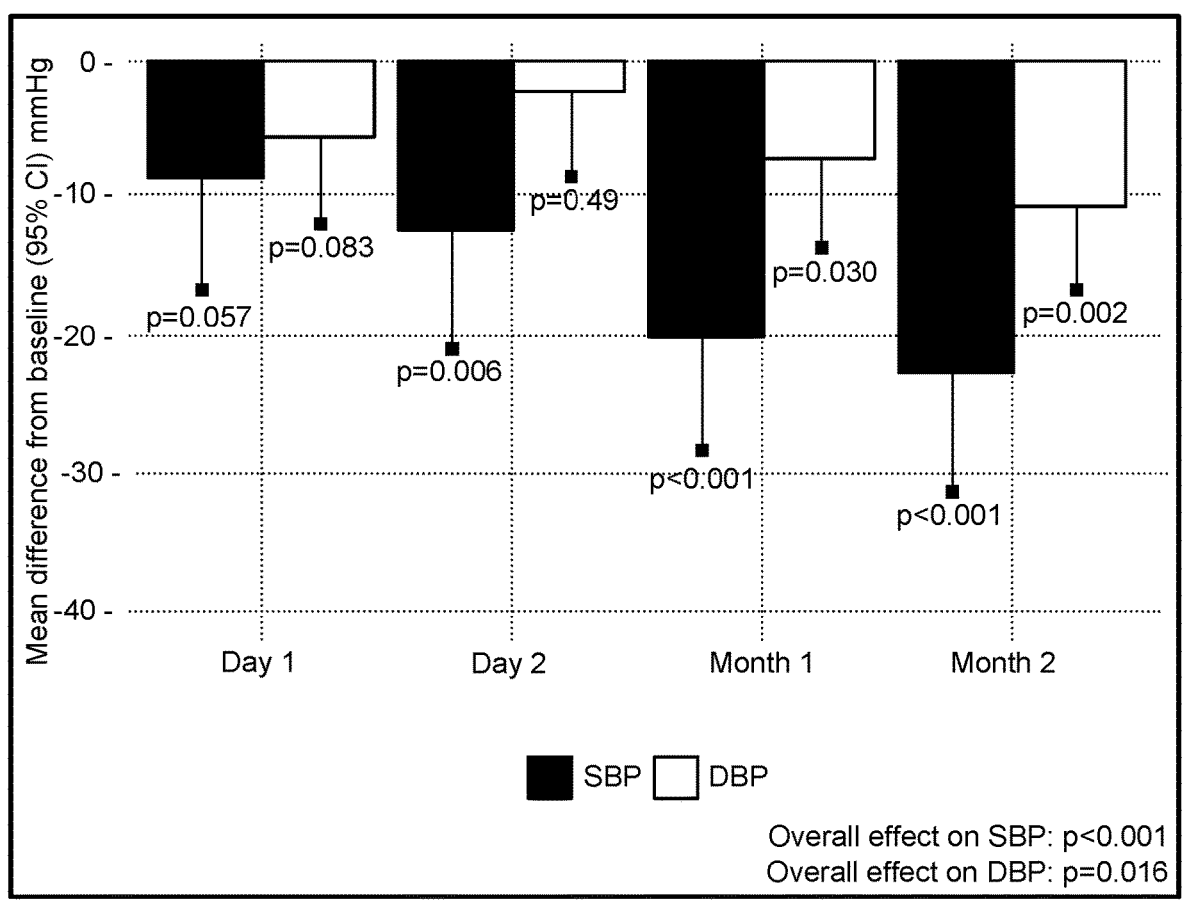
FIG. 13 is a bar chart showing change from baseline in office blood pressure (p-values for changes in systolic and diastolic blood pressure at each time point and for overall effects by linear mixed model analysis).
Figure 14:
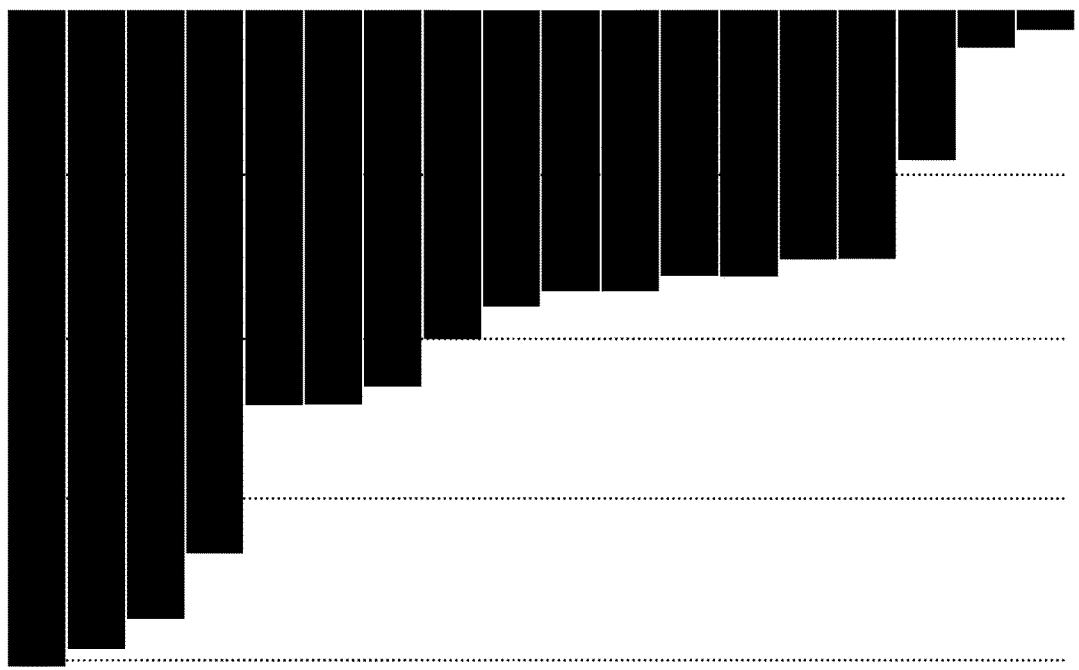
FIG. 14 shows waterfall plots of 24-hour ABPM (Ambulatory Blood Pressure Monitoring) changes for each subject at Month 2.

Office systolic blood pressure was reduced by 22.4 mm Hg (95% CI: −31.0, −13.8, p<0.001) 2 months post-procedure (FIG. 13). Office blood pressure measurements showed significant reductions at each assessment following renal pelvic denervation as early as one day post-procedure (FIG. 14). The decreases in office systolic blood pressure (p=0.002) and diastolic blood pressure (p=0.023) at day one post renal pelvic denervation were statistically significant by t-test but not by mixed model analysis (p=0.057 and p=0.083 for systolic blood pressure and diastolic blood pressure, respectively). By linear trend test from the time of the procedure to the 2-month endpoint, the progressive decrease in systolic blood pressure over time was statistically significant (p=0.001), whereas the decrease in diastolic blood pressure over time was not (v0.07).

By 2 months post procedure, mean daytime systolic blood pressure fell in 17 of 18 (94%) subjects and mean 24-hour systolic blood pressure fell in all 18 patients (FIG. 14). Mean daytime systolic blood pressure dropped by at least 5 mm Hg in 17 (94%) out of 18 subjects and in 16 (89%) out of 18 patients for 24-hour systolic blood pressure. Mean systolic blood pressure dropped at least 10 mm Hg in 16 (89%) of 18 patients during daytime systolic blood pressure and in 15 (83%) of 18 patients over mean 24 hours systolic blood pressure, and by at least 15 mm Hg in 12 (67%) of 18 patients during daytime systolic blood pressure and in 15 (83%) of 18 patients over mean 24 hours systolic blood pressure. No subjects experienced an increase in mean daytime or 24-hour systolic blood pressure at month 2 post renal pelvic denervation.

Office heart rate on the first day increased compared to baseline following renal pelvic denervation (p=0.03) but was lower at months 1 and 2 (p<0.07). Overall treatment effects of renal pelvic denervation resulted in a significant reduction in office heart rate (p<0.001) but no significant changes in heart rate were observed in mean daytime, nighttime or 24-hours levels.

Exploratory analysis of the response in subjects with (n=8) compared to those without (n=10) isolated systolic hypertension did not suggest differences between these groups in any measure of change in systolic blood pressure, diastolic blood pressure or heart rate (p=0.08 by Hotelling's T-statistic). Univariate analyses suggested smaller reduction in daytime and 24-hour diastolic blood pressure for subjects with isolated systolic hypertension. Two months following ablation in these subjects with isolated systolic hypertension, 24-hour systolic blood pressure dropped by 16.8 mm Hg (95% CI: −25.8 to −7.7, p=0.003 by t-test) and diastolic blood pressure dropped by 6.1 mm Hg (95% CI: −9.6 to −2.6, p=0.004 by t-test).

Effects on Laboratory Assessments. There was a small but significant increase in eGFR (6.3 mL/min/1.73 $m^2$ at month 1 and 7.2 mL/min/1.73 $m^2$ at month 2. p=0.033 by mixed model) and a significant decrease in mean serum creatinine (0.08 mg/dL both at months 1 and 2, p=0.023 by mixed model). Hemoglobin dropped by 0.5 g/dL by day 14, by 0.8 g/dL at month 1 and by 0.7 g/dL at month 2 (p=0.001 by mixed model). Hematocrit dropped by 2.4% (p=0.007 by mixed model) by month 2. No significant changes were noted in sodium and potassium levels.

Chronic kidney disease is typically classified by stages from stage 1 to stage 5. Generally, with all numbers expressed in units of mL/min/1.73 $m^2$, stage 1 is indicated by a GFR of 90 or above, stage 2 covers GFR in a range between 60 and 89, stage 3 covers GFR in a range between 30 and 59, stage 4 covers GFR in a range between 15 and 29, and stage 5 is classified as having a GFR below 15. Although patients at all stages can benefit from treatment as described herein, treatment is particularly beneficial for patients at stages 3-5.

It is believed that, other than eGFR/GFR, there are other markers typically associated with kidney disease that can be used to select subjects for treatment according to embodiments herein, and that will respond positively to treatment. For instance, one indicator associated with kidney damage is the presence of albumin in a urine sample. This indicator may show that kidney issues exist even when eGFR is in a normal, stage 1, or stage 2 range. In a normally functioning kidney, little to no protein/albumin is passed from the blood to the urine by the glomerular capsules in the kidney. In a damaged kidney and/or due to high blood pressure, the glomerular capsules may to some extent be unable to prevent the passage of protein/albumin from the blood to the urine. This condition is known as albuminuria or proteinuria. It is a symptom associated with many different types of kidney disease and can be a significant risk factor for complications.

In an embodiment, one or more methods for measuring albumin is performed on a candidate. One known method is a dipstick method, where the candidate's urine is reacted with a stick that changes color to indicate protein levels in the urine. Another method collects a candidate's 24-hour production of urine and measures the amount of protein excreted in the urine over that timeframe. A normal range of albumin in the urine by this measure is <150 mg/day. Proteinuria is generally indicated when albumin levels exceed 500 mg/day, and levels that exceed 3.5 g/day are indicative of nephrotic syndrome. Where creatinine is also measured, another marker can be developed using the ratio of albumin to creatinine in a sample.

In an embodiment, efficacy of treatment can be measured by taking a baseline proteinuria reading, which may be used alone or in combination with other metabolic indicators to screen candidates "in" or "out" for treatment. At one or more timeframes after treatment (e.g., two weeks, one month, two months, six months, or twelve months), a second proteinuria reading is taken and compared to the baseline reading. A decrease in albumin measure should be expected when a patient responds positively to treatment.

All of the functionalities described in connection with one embodiment are intended to be applicable to other embodiments except where expressly stated to the contrary or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method for reducing blood pressure in a patient diagnosed with hypertension by altering efferent (inbound) renal nerve activity via a procedure that disrupts renal afferent (outbound) nerves, the method comprising:
   advancing a catheter through a urinary tract of a patient toward a renal pelvis of the patient such that a distal end of the catheter is positioned within the renal pelvis or ureteral pelvic junction adjacent the renal pelvis;
   providing a plurality of electrodes at the distal end of the catheter, the electrodes in communication with a radio frequency energy source;
   drawing a vacuum through the catheter to collapse a wall of the renal pelvis such that renal pelvic wall tissue of the renal pelvis is in contact with the plurality of electrodes; and
   applying radio frequency energy to the plurality of electrodes to disrupt and/or ablate afferent nerves in the renal pelvic wall tissue proximate the respective locations at which the renal pelvic wall tissue contacts each of the plurality of electrodes;
   wherein applying radio frequency energy disrupts and/or ablates primarily afferent renal nerves contained in the renal pelvic wall tissue;
   whereby, by disrupting and/or ablating the primarily afferent renal nerves, the patient's efferent nerve activity is altered; and
   whereby altering the patient's efferent nerve activity causes a reduction in the patient's blood pressure.

2. The method of claim 1, wherein the radio frequency energy is applied for 1 to 2 minutes.

3. The method of claim 1, wherein the renal pelvic wall tissue containing the afferent renal nerves is heated to a temperature of 45 to 80 degrees Celsius.

4. The method of claim 1, wherein at least a portion of the disrupted and/or ablated afferent renal nerves are located within one or more smooth muscle layers of the renal pelvic wall.

5. The method of claim 4, wherein at least a portion of the disrupted and/or ablated afferent renal nerves are located within an endothelium region of the renal pelvic wall.

6. The method of claim 1, wherein disrupting and/or ablating afferent renal nerves has a direct effect on efferent renal nerve activity.

7. The method of claim 1, wherein applying radio frequency energy forms lesions in renal pelvic wall tissue by raising the temperature of the one or more electrodes to 60 Degrees C. for two minutes.

8. The method of claim 1, wherein the patient's renal pelvis contains urine prior to the application of the vacuum.

9. The method of claim 1, wherein the vacuum is drawn through a lumen of the catheter.

10. The method of claim 1, wherein collapse of walls of the renal pelvis is partial.

11. The method of claim 1, wherein applying radio frequency energy preferentially disrupts and/or ablates nerves disposed closer to an interior surface of the wall of the renal pelvis than to an exterior surface of the wall of the renal pelvis.

\* \* \* \* \*